(12) United States Patent
Jackson et al.

(10) Patent No.: US 12,053,217 B2
(45) Date of Patent: Aug. 6, 2024

(54) RECEIVER ASSEMBLY WITH ROTATION BLOCKING SIDE POCKETS FOR TWIST-IN-PLACE INSERT AND METHOD OF ASSEMBLY

(71) Applicant: Roger P. Jackson, Prairie Village, KS (US)

(72) Inventors: Roger P. Jackson, Prairie Village, KS (US); James L. Surber, Kansas City, KS (US); Nathaniel D. Ginzton, Boise, ID (US)

(*) Notice: Subject to any disclaimer, the term of this patent is extended or adjusted under 35 U.S.C. 154(b) by 0 days.

(21) Appl. No.: 18/364,168

(22) Filed: Aug. 2, 2023

(65) Prior Publication Data

US 2023/0371994 A1 Nov. 23, 2023

Related U.S. Application Data

(63) Continuation of application No. 17/840,457, filed on Jun. 14, 2022, now Pat. No. 11,730,526, which is a continuation of application No. PCT/US2020/065720, filed on Dec. 17, 2020.

(60) Provisional application No. 62/949,291, filed on Dec. 17, 2019.

(51) Int. Cl.
  *A61B 17/70* (2006.01)
  *A61B 17/86* (2006.01)
  *A61B 17/00* (2006.01)

(52) U.S. Cl.
  CPC ...... *A61B 17/8685* (2013.01); *A61B 17/7032* (2013.01); *A61B 17/7037* (2013.01); *A61B 2017/00477* (2013.01)

(58) Field of Classification Search
  CPC .............. A61B 17/7032–7038; A61B 17/7001
  See application file for complete search history.

(56) References Cited

U.S. PATENT DOCUMENTS

| 5,669,911 A | 9/1997 | Errico et al. |
| 5,672,176 A | 9/1997 | Biedermann et al. |
| 5,690,630 A | 11/1997 | Errico et al. |
| (Continued) | | |

FOREIGN PATENT DOCUMENTS

WO  WO 2020/056385  3/2020

OTHER PUBLICATIONS

U.S. Appl. No. 18/359,566, filed Jul. 26, 2023.

*Primary Examiner* — Lynnsy M Summitt
(74) *Attorney, Agent, or Firm* — Polsinelli PC

(57) ABSTRACT

A receiver assembly includes a receiver with a central bore and a bottom opening, a channel for receiving a rod, and a discontinuous horizontal recess and one or more vertically-aligned side pockets formed into sidewall surfaces of the central bore. The assembly also includes a pressure insert with an upwardly-open rod-seating surface, opposite flanges projecting radially outward from an upper portion of an outer cylindrical surface, and one or more side protuberances projecting radially outward below the opposite flanges. The pressure insert is positionable into the central bore in a first position and then rotatable from the first position to a second position in which the side protuberances are interferingly forced into the side pocket recesses to inhibit further rotation of the pressure insert and the opposite flanges are rotated under downwardly-facing surfaces of the horizontal recess to inhibit upward movement of the pressure insert within the central bore.

28 Claims, 23 Drawing Sheets

(56) References Cited

U.S. PATENT DOCUMENTS

| | | |
|---|---|---|
| 5,782,833 A | 7/1998 | Haider |
| 5,797,911 A | 8/1998 | Sherman et al. |
| 5,885,286 A | 3/1999 | Sherman et al. |
| 6,010,503 A | 1/2000 | Richelsoph et al. |
| 6,063,090 A | 5/2000 | Schläpfer |
| 6,090,111 A | 7/2000 | Nichols |
| 6,254,602 B1 | 7/2001 | Justis |
| 6,280,442 B1 | 8/2001 | Barker et al. |
| 6,355,040 B1 | 3/2002 | Richelsoph et al. |
| 6,471,705 B1 | 10/2002 | Biedermann et al. |
| 6,485,491 B1 | 11/2002 | Farris et al. |
| 6,485,494 B1 | 11/2002 | Haider |
| 6,530,929 B1 | 3/2003 | Justis et al. |
| 6,540,748 B2 | 4/2003 | Lombardo |
| 6,565,565 B1 | 5/2003 | Yuan et al. |
| 6,626,908 B2 | 9/2003 | Cooper et al. |
| 6,740,086 B2 | 5/2004 | Richelsoph |
| 6,835,196 B2* | 12/2004 | Biedermann ...... A61B 17/7037 606/308 |
| 6,837,889 B2 | 1/2005 | Shluzas |
| 6,905,500 B2 | 6/2005 | Jeon et al. |
| 6,945,975 B2 | 9/2005 | Dalton |
| 7,066,937 B2 | 6/2006 | Shluzas |
| 7,087,057 B2 | 8/2006 | Konieczynski et al. |
| 7,141,051 B2 | 11/2006 | Janowski et al. |
| 7,144,396 B2 | 12/2006 | Shluzas |
| 7,163,539 B2 | 1/2007 | Abdelgany et al. |
| 7,264,621 B2 | 9/2007 | Coates et al. |
| 7,306,606 B2* | 12/2007 | Sasing ............... A61B 17/7037 606/279 |
| 7,311,712 B2 | 12/2007 | Dalton |
| 7,377,923 B2 | 5/2008 | Purcell et al. |
| 7,445,627 B2 | 11/2008 | Hawkes et al. |
| 7,604,655 B2 | 10/2009 | Warnick |
| 7,686,834 B2 | 3/2010 | Saint Martin |
| 7,686,835 B2 | 3/2010 | Warnick |
| 7,695,497 B2 | 4/2010 | Cordaro et al. |
| 7,766,915 B2 | 8/2010 | Jackson |
| 7,766,945 B2 | 8/2010 | Nilsson et al. |
| 7,776,067 B2 | 8/2010 | Jackson |
| 7,789,896 B2 | 9/2010 | Jackson |
| 7,789,900 B2 | 9/2010 | Levy et al. |
| 7,811,310 B2 | 10/2010 | Baker et al. |
| 7,833,250 B2* | 11/2010 | Jackson ............. A61B 17/7028 606/270 |
| 7,833,251 B1 | 11/2010 | Ahlgren et al. |
| 7,842,073 B2 | 11/2010 | Richelsoph et al. |
| 7,901,436 B2 | 3/2011 | Baccelli |
| 7,909,830 B2 | 3/2011 | Frigg et al. |
| 7,914,536 B2 | 3/2011 | MacDonald et al. |
| 7,942,909 B2 | 5/2011 | Hammill, Sr. et al. |
| 7,947,065 B2 | 5/2011 | Hammill, Sr. et al. |
| 7,951,173 B2 | 5/2011 | Hammill, Sr. et al. |
| 7,967,850 B2 | 6/2011 | Jackson |
| 7,988,694 B2 | 8/2011 | Barrus et al. |
| 8,021,397 B2 | 9/2011 | Farris et al. |
| 8,034,089 B2* | 10/2011 | Matthis ............. A61B 17/7076 606/306 |
| 8,048,112 B2 | 11/2011 | Suzuki et al. |
| 8,066,744 B2 | 11/2011 | Justis et al. |
| 8,075,603 B2 | 12/2011 | Hammill, Sr. et al. |
| 8,083,776 B2 | 12/2011 | Alvarez |
| 8,197,517 B1 | 6/2012 | Lab et al. |
| 8,197,518 B2 | 6/2012 | Hammill, Sr. et al. |
| 8,221,472 B2 | 7/2012 | Peterson et al. |
| 8,303,602 B2* | 11/2012 | Biedermann ...... A61B 17/7037 606/104 |
| 8,308,782 B2 | 11/2012 | Jackson |
| 8,353,932 B2 | 1/2013 | Jackson |
| 8,361,123 B2 | 1/2013 | Fanger et al. |
| 8,382,805 B2 | 2/2013 | Wang et al. |
| 8,398,683 B2 | 3/2013 | Berrevoets et al. |
| 8,439,922 B1 | 5/2013 | Arnold et al. |
| 8,449,578 B2 | 5/2013 | Keiser et al. |
| 8,556,938 B2* | 10/2013 | Jackson ............. A61B 17/7008 606/264 |
| 8,562,652 B2 | 10/2013 | Biedermann et al. |
| 8,628,558 B2 | 1/2014 | Harvey et al. |
| 8,663,290 B2 | 3/2014 | Doubler et al. |
| 8,663,291 B2 | 3/2014 | Doubler et al. |
| 8,663,298 B2 | 3/2014 | Keyer et al. |
| 8,696,712 B2 | 4/2014 | Biedermann et al. |
| 8,814,911 B2* | 8/2014 | Jackson ............... A61B 17/705 606/264 |
| 8,876,869 B1* | 11/2014 | Schafer ............. A61B 17/7032 606/86 A |
| 8,882,817 B2* | 11/2014 | Jones ................. A61B 17/7037 606/267 |
| 8,888,827 B2 | 11/2014 | Harper et al. |
| 8,926,671 B2 | 1/2015 | Biedermann et al. |
| 8,986,349 B1* | 3/2015 | German ............. A61B 17/7037 606/279 |
| 8,998,959 B2 | 4/2015 | Jackson et al. |
| 9,044,272 B2 | 6/2015 | Shaffrey et al. |
| 9,060,814 B2 | 6/2015 | Doubler et al. |
| 9,078,705 B2* | 7/2015 | Matthis ............. A61B 17/7002 |
| 9,119,674 B2* | 9/2015 | Matthis ............. A61B 17/8685 |
| 9,155,567 B2 | 10/2015 | Auerbach et al. |
| 9,198,695 B2 | 12/2015 | Shluzas et al. |
| 9,254,150 B2* | 2/2016 | Biedermann ...... A61B 17/7082 |
| 9,259,247 B2* | 2/2016 | Chandanson ...... A61B 17/7032 |
| 9,358,047 B2 | 6/2016 | Mishra et al. |
| 9,439,680 B2 | 9/2016 | Biedermann et al. |
| 9,486,246 B2* | 11/2016 | Biedermann ...... A61B 17/7037 |
| 9,492,204 B2 | 11/2016 | Biedermann et al. |
| 9,526,529 B2* | 12/2016 | Charvet ............. A61B 17/7037 |
| 9,572,600 B2 | 2/2017 | Biedermann et al. |
| 9,615,858 B2 | 4/2017 | Doubler et al. |
| 9,649,134 B2* | 5/2017 | Hannen ............. A61B 17/7032 |
| 9,655,652 B2 | 5/2017 | Biedermann et al. |
| 9,707,013 B2 | 7/2017 | Rezach et al. |
| 9,763,702 B2 | 9/2017 | Schlaepfer et al. |
| D799,949 S | 10/2017 | Stevenson et al. |
| 9,775,660 B2* | 10/2017 | Spratt ................. A61B 17/8685 |
| 9,848,892 B2* | 12/2017 | Biedermann ...... A61B 17/1659 |
| 9,924,975 B2 | 3/2018 | Jackson et al. |
| 9,980,753 B2* | 5/2018 | Jackson ............. A61B 17/7037 |
| 10,028,770 B2 | 7/2018 | Rezach et al. |
| 10,039,572 B2 | 8/2018 | Harris et al. |
| 10,058,354 B2* | 8/2018 | Jackson ............. A61B 17/863 |
| 10,064,657 B2 | 9/2018 | Spitler |
| 10,064,658 B2 | 9/2018 | Jackson et al. |
| 10,117,680 B2* | 11/2018 | Trautwein .......... A61B 17/7037 |
| 10,154,859 B2 | 12/2018 | Keyer et al. |
| 10,172,647 B2 | 1/2019 | Elsbury |
| 10,188,432 B2 | 1/2019 | Jackson et al. |
| 10,194,951 B2 | 2/2019 | Jackson et al. |
| 10,285,738 B1 | 5/2019 | Doubler et al. |
| 10,335,203 B2 | 7/2019 | Fiechter et al. |
| 10,363,070 B2* | 7/2019 | Jackson ............. A61B 17/7037 |
| 10,463,402 B2* | 11/2019 | Biester ............... A61B 17/7007 |
| 10,485,594 B2 | 11/2019 | Toon et al. |
| 10,507,043 B1 | 12/2019 | Gladieux |
| 10,517,645 B2 | 12/2019 | van der Pol |
| 10,695,100 B2 | 6/2020 | May et al. |
| 10,765,455 B2 | 9/2020 | Jackson et al. |
| 10,792,074 B2 | 10/2020 | Jackson |
| 11,020,150 B1 | 6/2021 | Doubler et al. |
| 11,134,993 B2* | 10/2021 | Jackson ............. A61B 17/7035 |
| 11,141,199 B1 | 10/2021 | Doubler et al. |
| 11,234,738 B2 | 2/2022 | Jackson et al. |
| 11,234,745 B2 | 2/2022 | Jackson |
| 11,304,732 B2 | 4/2022 | Mueller et al. |
| 11,464,549 B2* | 10/2022 | Jackson ............. A61B 17/8685 |
| 11,571,244 B2 | 2/2023 | Loftis et al. |
| 2003/0149431 A1 | 8/2003 | Varieur |
| 2004/0102781 A1 | 5/2004 | Jeon |
| 2004/0260283 A1 | 12/2004 | Wu et al. |
| 2005/0203516 A1 | 9/2005 | Biedermann et al. |
| 2005/0261687 A1 | 11/2005 | Garamszegi et al. |
| 2006/0161152 A1 | 7/2006 | Ensign et al. |
| 2006/0217716 A1 | 9/2006 | Baker et al. |
| 2007/0118123 A1 | 5/2007 | Strausbaugh et al. |

(56) References Cited

U.S. PATENT DOCUMENTS

| | | | |
|---|---|---|---|
| 2007/0270813 A1* | 11/2007 | Garamszegi | A61B 17/7032 606/278 |
| 2009/0204155 A1* | 8/2009 | Aschmann | A61B 17/7032 606/301 |
| 2010/0152787 A1 | 6/2010 | Walsh et al. | |
| 2010/0298891 A1* | 11/2010 | Jackson | A61B 17/7008 606/305 |
| 2010/0331887 A1 | 12/2010 | Jackson et al. | |
| 2012/0310284 A1 | 12/2012 | Gerchow | |
| 2013/0103098 A1 | 4/2013 | Jackson et al. | |
| 2013/0218213 A1 | 8/2013 | Lemoine | |
| 2014/0025119 A1* | 1/2014 | Biedermann | A61B 17/7032 606/266 |
| 2014/0121703 A1* | 5/2014 | Jackson | A61B 17/863 606/246 |
| 2023/0172641 A1* | 6/2023 | Haschtmann | A61B 17/705 606/266 |

* cited by examiner

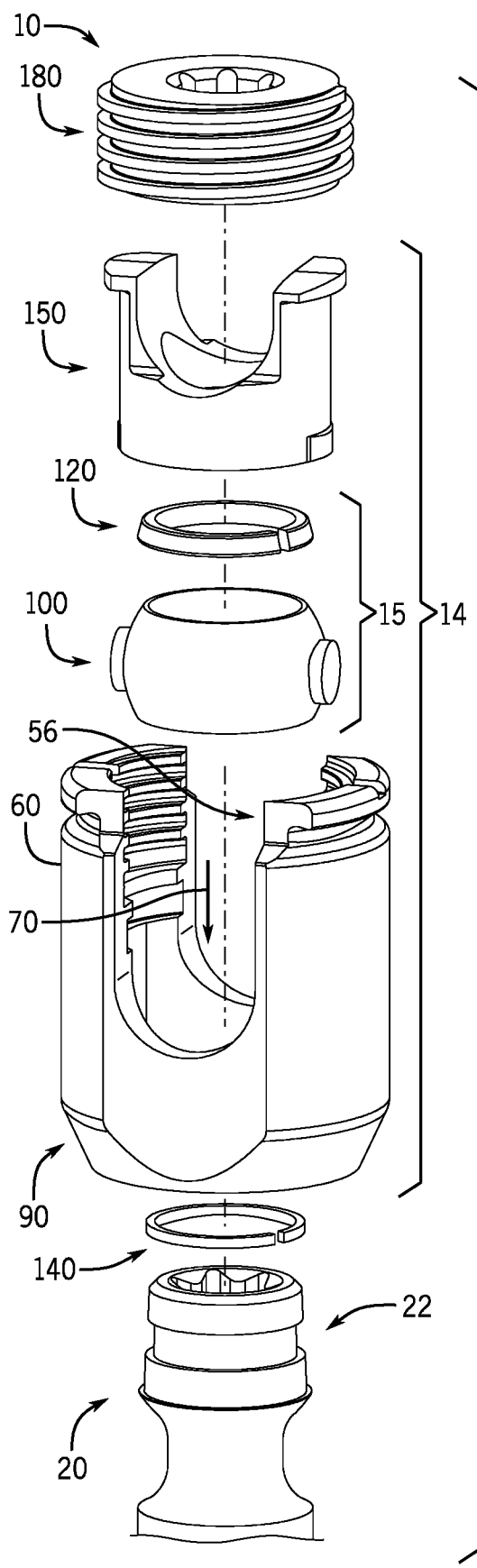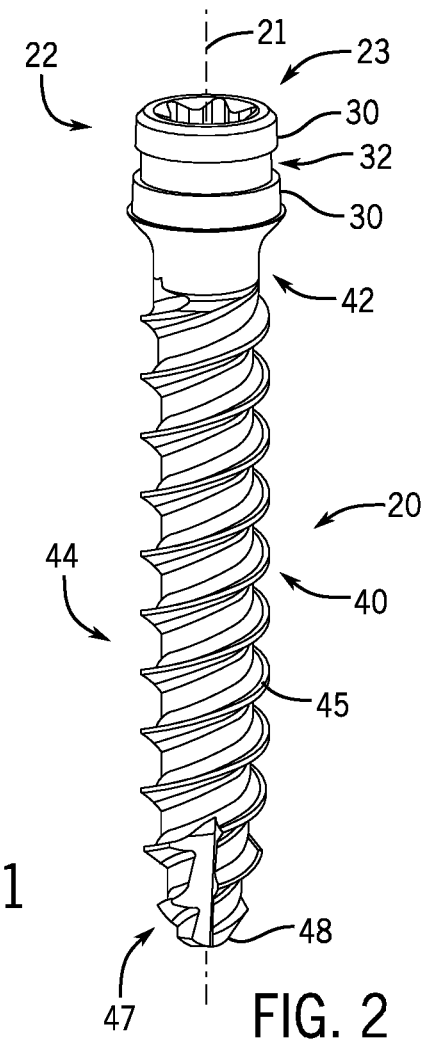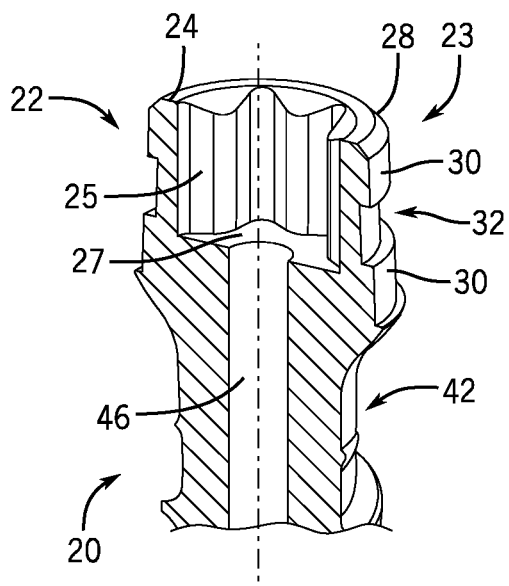
FIG. 1
FIG. 2
FIG. 3

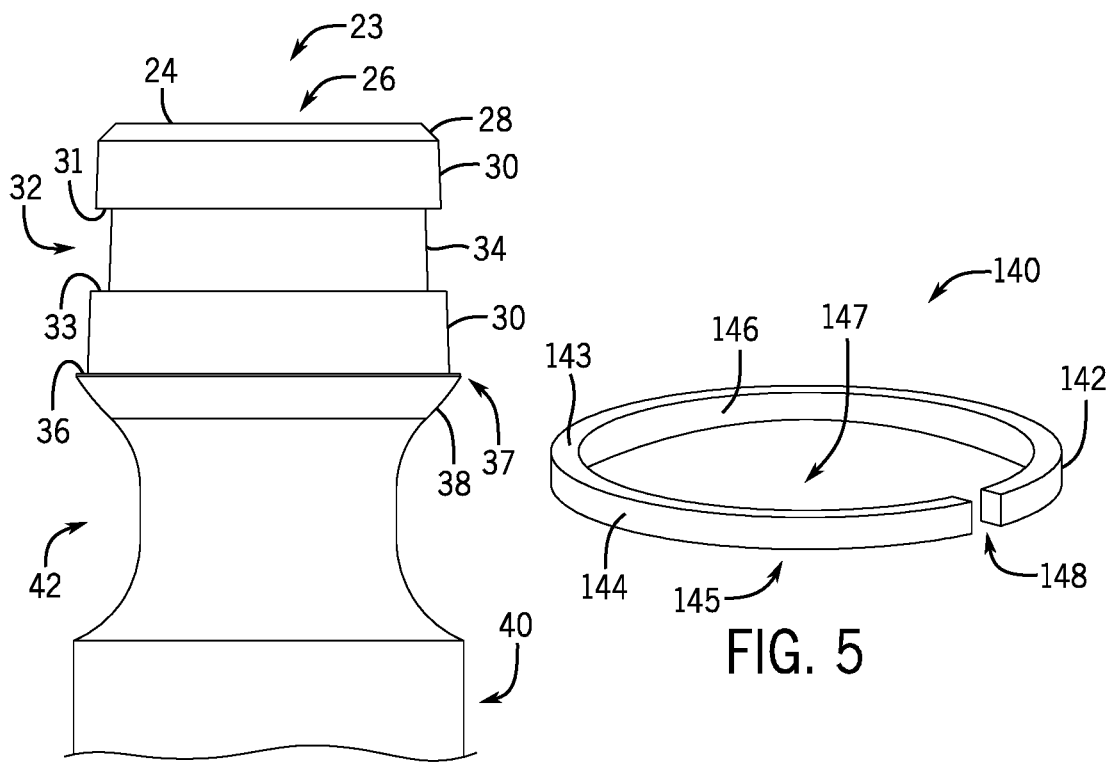
FIG. 4
FIG. 5
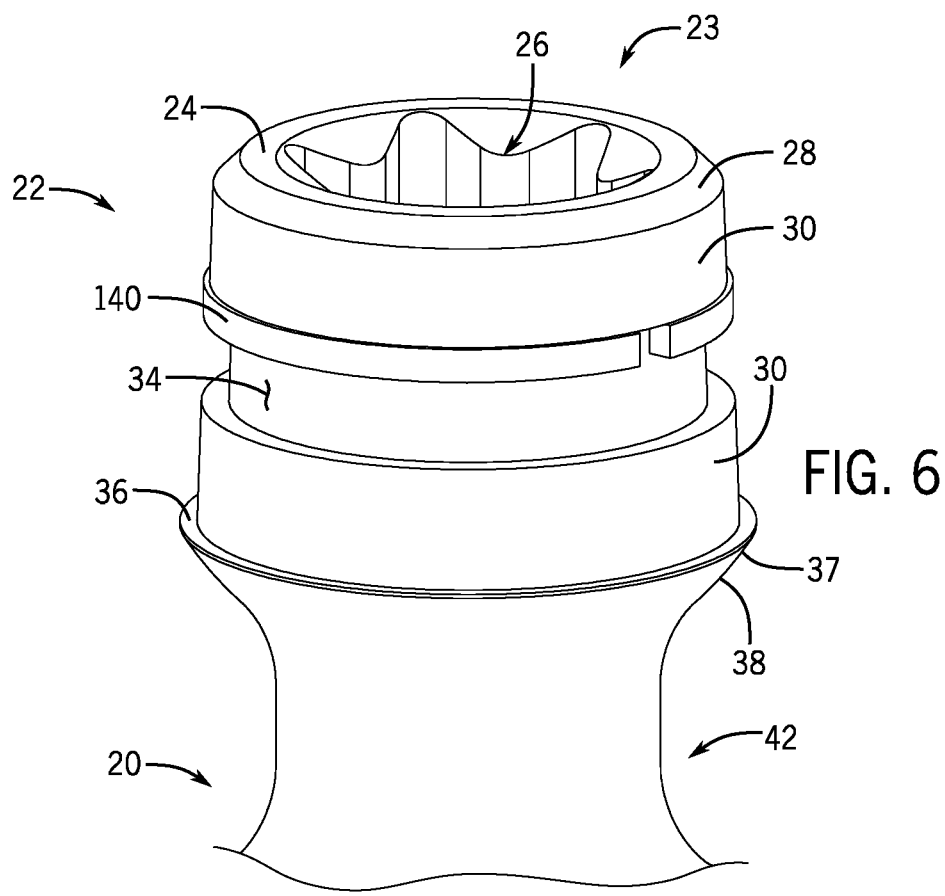
FIG. 6

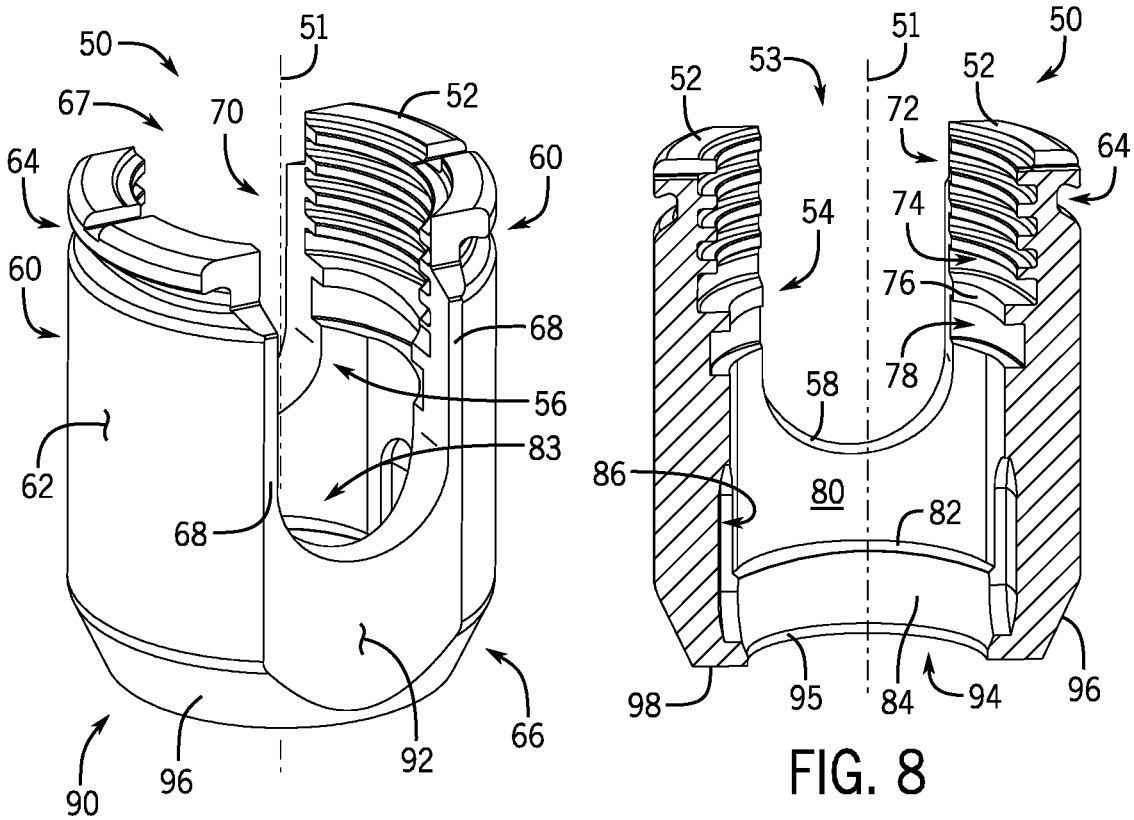
FIG. 7
FIG. 8
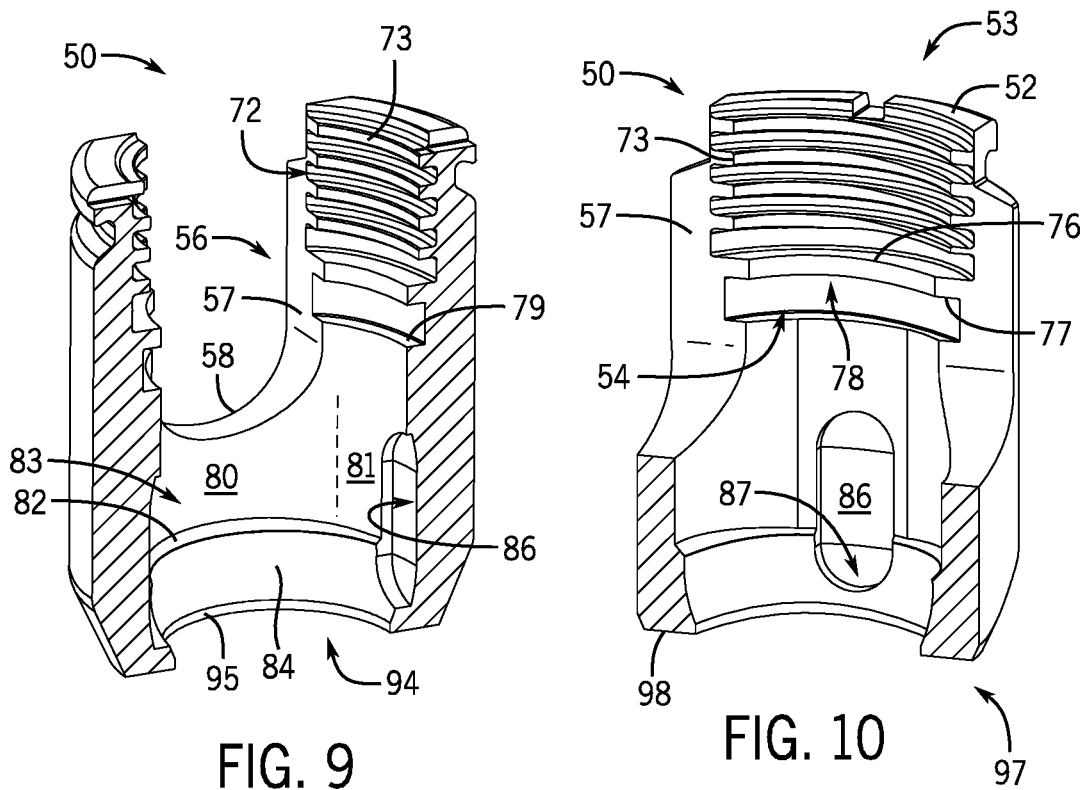
FIG. 9
FIG. 10

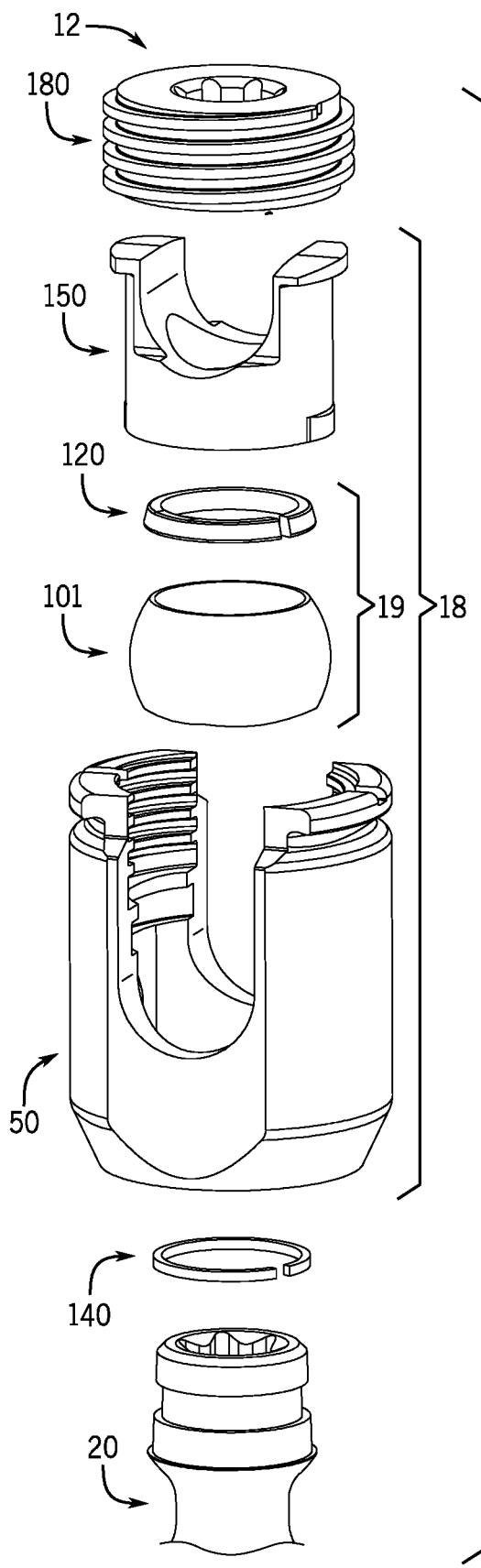
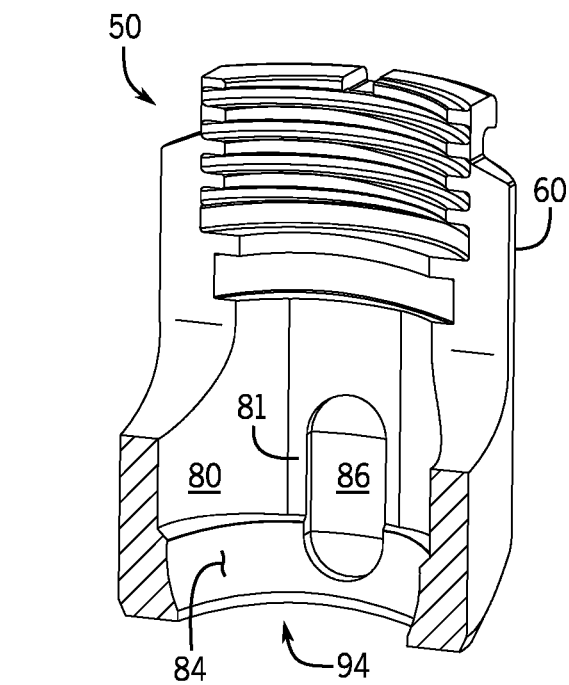
FIG. 66
FIG. 65
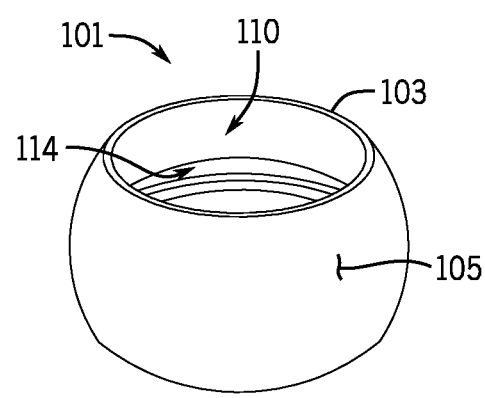
FIG. 67

RECEIVER ASSEMBLY WITH ROTATION BLOCKING SIDE POCKETS FOR TWIST-IN-PLACE INSERT AND METHOD OF ASSEMBLY

CROSS-REFERENCE TO RELATED APPLICATIONS

This application is a continuation of U.S. application Ser. No. 17/840,457, filed Jun. 14, 2022, which is a continuation of PCT/US2020/065720, filed Dec. 17, 2020, which claims the benefit of U.S. Provisional Application No. 62/949,291, filed Dec. 17, 2019, each of which is incorporated by reference in its entirety herein, and for all purposes.

FIELD

The present disclosure relates generally to pivotal bone anchor assemblies and their use in spinal surgery involving vertebral stabilization.

BACKGROUND

The configuration and complexity of the spine and pelvis is well described in the art. For example, multiple types of implants or spinal fixation devices, such as rods, screws and hooks, and their variations have been developed for insertion into and onto the spine and pelvis for the purpose of treating spinal disorders, such as degenerative conditions and deformities. Due to these spinal disorders, surgeons can encounter considerable difficulty when attempting to insert such implant devices into and onto the spine and pelvis. Due to their size, the receivers of the implants frequently get in the way of the work that must be done after they are inserted when the implant devices can only be attached to the bony anatomy as a complete unit. As in the case of correcting a spinal deformity, for example, the surgeon must often commit to attaching multi-planar or mono-planar screws (also known as screw assemblies) at predetermined levels along the region of the spine that is to be realigned or corrected and stabilized prior to fusion. Sometimes, however, the surgeon may wish to change the strategy or techniques to be applied in the procedure after the screws have been placed. This is to say that it may become desirable during surgery that one or more multi-planar screws be changed out for a mono-planar screw, or vice versa. The same can be said for hooks. However, removing the implanted device and replacing it with another takes time and can weaken the purchase of the bone anchor in the bone or cause other problems, such as unwanted bore penetrations, and fracturing.

Consequently, a need exists for a method and apparatus that provides for the modification of a surgical procedure by easily changing the planned selection of multi-planar screw assemblies to mono-planar screw assemblies, and vice versa, after placement of the bone anchors. It is toward such a method and apparatus that the present disclosure is directed.

SUMMARY

The present disclosure relates generally systems and associated methods related to performing spinal fixation surgeries with the use of bone anchor assemblies having bone attachment structures, such as screws, shanks and hooks, which can be bottom loaded into receivers, housings or heads, wherein the receivers and at least some of their associated internal components can rotate or pivot in different selected directions, along with the bone attachment structures, relative to their receivers. More specifically, receivers that are configured to provide different functionalities, such as independent locking, can be pre-assembled with their internal components into receiver sub-assemblies that are configured to be snapped on the upper end capture portion of the bone attachment structures. This allows for the bone attachment structures to be affixed to the bony anatomy either before or after being snapped into their respective pivoting receiver sub-assemblies.

Due to the reasons discussed above, moreover, it can be desirable to insert the bone attachment structures into the spine independent of their larger and somewhat bulky receiver sub-assemblies, and decide later on in the procedure where exactly multi-planar implants and/or mono-planar implants should be placed. Accordingly, one aspect the spinal fixation system described herein is directed toward eliminating or at least improving upon the shortcomings of the prior part through the introduction of a bone attachment structure having an upper end capture structure comprising a "universal" shank head. In particular, and as further disclosed in greater detail below, the type of "universal" shank head of the present disclosure is configured to be snapped onto and captured by either a multi-planar pivoting receiver sub-assembly or a mono-planar pivoting receiver sub-assembly. Additional benefits of such a spinal fixation system will also be appreciated by one skilled in the art, including but not limited to increased savings afforded by modular component designs that allow for common components to be shared between the different types of receiver sub-assemblies, fewer implants needing to be maintained in inventory, accounted for, and being shipped to and from hospitals and surgery centers, reduced overall costs, and other benefits yet to be realized, such as more efficient spine surgeries and improved outcomes.

Another aspect of the spinal fixation system comprises a pivotal bone anchor assembly that includes a bone anchor or shank having a capture portion with a frusto-conical outer surface and a horizontal capture recess extending into and circumferentially around a mid-portion thereof. The assembly also includes a receiver having a central bore with a seating surface proximate a bottom opening, as well as a closed ring retainer having both a retainer aperture with a tapered inner surface that is slidably engageable with the frusto-conical surface of the capture structure of the bone anchor, and an internal retainer aperture recess that extends into and circumferentially around the tapered inner surface. The assembly further includes a snap ring having a snap ring aperture that is smaller than the retainer aperture, and which is positionable within the retainer aperture recess prior to assembly of the closed ring retainer within the receiver. Upon securing the closed ring retainer with the enclosed snap ring within the central bore of the receiver, with the retainer aperture centered above the bottom opening, the capture portion of the bone anchor is uploadable into the retainer aperture with the frusto-conical surface of the capture portion engaging and continuously expanding the snap ring until the horizontal capture recess reaches the retainer aperture recess, at which point the snap ring snaps into the horizontal capture recess to couple the bone anchor to the closed ring retainer and the receiver.

The invention will be better understood upon review of the detailed description set forth below taken in conjunction with the accompanying drawing figures, which are briefly described as follows.

BRIEF DESCRIPTION OF THE DRAWINGS

FIG. 1 is an exploded perspective view of a mono-planar embodiment of a pivotal bone anchor assembly, in accordance with a representative embodiment of the present disclosure.

FIG. 2 is a perspective view of the bone anchor of the pivotal bone anchor assembly of FIG. 1.

FIG. 3 is a cross-sectional perspective view of the capture portion of the bone anchor of FIG. 2.

FIG. 4. is a side view of the capture portion of the bone anchor of FIG. 2.

FIG. 5 is a perspective view of the scraper ring of the pivotal bone anchor assembly of FIG. 1.

FIG. 6 is a perspective side view of the capture portion of FIG. 4 and the scraper ring of FIG. 5 after assembly together.

FIG. 7 is a perspective view of the receiver of the pivotal bone anchor assembly of FIG. 1.

FIG. 8 is a cross-sectional side view of the receiver of FIG. 7.

FIG. 9 is a cross-sectional perspective view of the receiver of FIG. 7.

FIG. 10 is another cross-sectional perspective view of the receiver of FIG. 7.

FIG. 65 is an exploded perspective view of a multi-planar embodiment of the pivotal bone anchor assembly, in accordance with another representative embodiment of the present disclosure.

FIG. 66 is a cross-sectional perspective view of the receiver of the pivotal bone anchor assembly of FIG. 65.

FIG. 67 is a perspective view of the closed ring retainer of the pivotal bone anchor assembly of FIG. 65.

Figure 11:
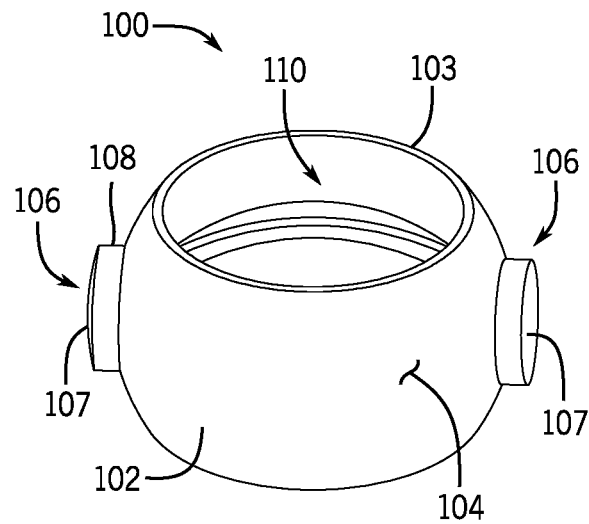
FIG. 11 is a perspective view of the closed ring retainer of the pivotal bone anchor assembly of FIG. 1.
Figure 12:
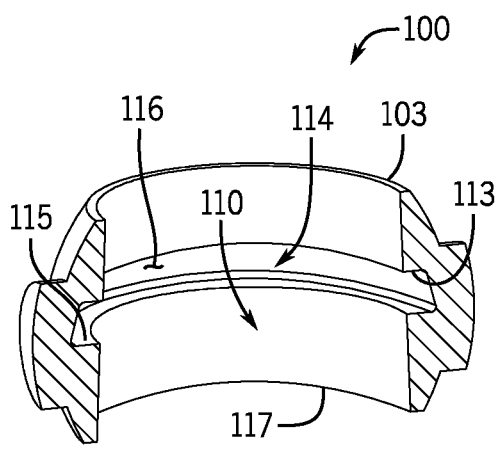
FIG. 12 is a cross-sectional perspective view of the closed ring retainer of FIG. 11.
Figure 13:
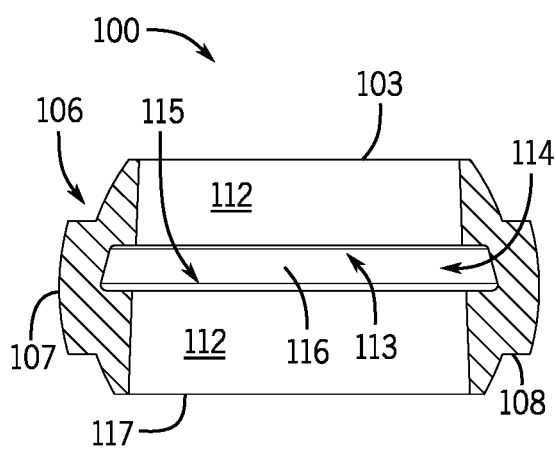
FIG. 13 is a cross-sectional side view of the closed ring retainer of FIG. 11.
Figure 14:
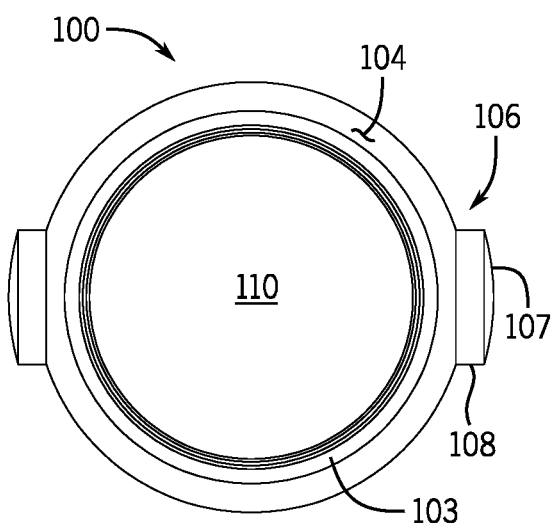
FIG. 14 is a top view of the closed ring retainer of FIG. 11
Figure 15:
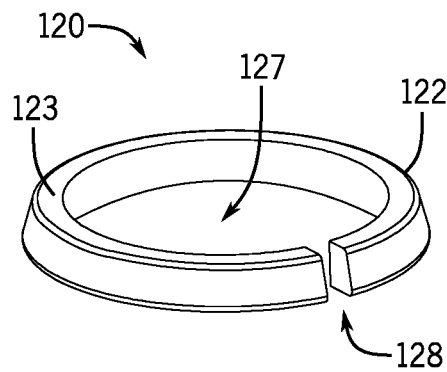
FIG. 15 is a top perspective view of the snap ring of the pivotal bone anchor assembly of FIG. 1.
Figure 16:
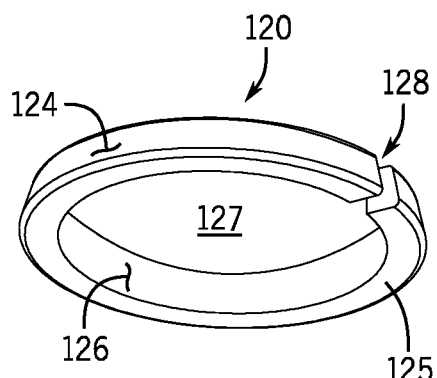
FIG. 16 is a bottom perspective view of the snap ring of FIG. 15.
Figure 17:
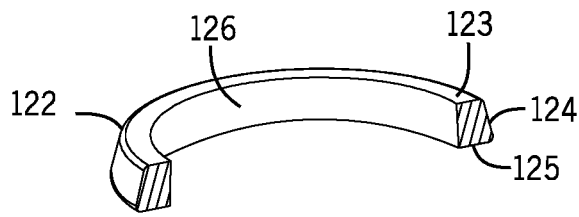
FIG. 17 is a cross-sectional perspective view of the snap ring of FIG. 15.

Those skilled in the art will appreciate and understand that, according to common practice, various features and elements of the drawings described above are not necessarily drawn to scale, and that the dimensions and relative positions between the features or elements may be expanded, reduced or otherwise altered to more clearly illustrate the various embodiments of the present disclosure depicted therein.

DESCRIPTION OF THE INVENTION

The following description, in conjunction with the accompanying drawings described above, is provided as an enabling teaching of exemplary embodiments of both pivotal and non-pivotal bone anchor assemblies found in a spinal fixation system, together with methods for assembling and using the bone anchor assemblies as a system to secure an elongate rod to patient bone in spinal surgery. As described below, the individual bone anchor assemblies, system, and/or methods of the present disclosure can provide several significant advantages and benefits over other pivotal and/or non-pivotal bone anchors and spinal fixation systems known in the art. The recited advantages are not meant to be limiting in any way, however, as one skilled in the art will appreciate that other advantages may also be realized upon practicing the present disclosure.

Furthermore, those skilled in the relevant art will recognize that changes can be made to the described embodiments while still obtaining the beneficial results. It will also be apparent that some of the advantages and benefits of the described embodiments can be obtained by selecting some of the features of the embodiments without utilizing other features, and that features from one embodiment may be interchanged or combined with features from other embodiments in any appropriate combination. For example, any individual or collective features of method embodiments may be applied to apparatus, product or system embodiments, and vice versa. Likewise, structural elements or functional features from one embodiment may also be combined with or replaced by structural elements or functional features from one or more additional embodiments in any suitable manner. Those who work in the art will therefore recognize that many modifications and adaptations to the embodiments described are possible and may even be desirable in certain circumstances, and are a part of the disclosure. Thus, the present disclosure is provided as an illustration of the principles of the embodiments and not in limitation thereof, since the scope of the invention is to be defined by the claims.

One embodiment of a pivotal bone anchor assembly shown in FIG. 1, and further described in reference to FIGS. 2-62, includes components having features or aspects configured to limit the pivoting motion of the bone anchor relative to the receiver sub-assembly (or vice versa) to a single plane, hereinafter interchangeably referenced as a uni-planar or 'mono-planar' embodiment. Another embodiment 12 of a pivotal bone anchor assembly shown in FIG. 65, and further described in reference to FIGS. 66-69, includes alternative components having features or aspects configured to provide pivoting motion of the bone anchor relative to the receiver sub-assembly around a 360-degree range, hereinafter interchangeably referenced to as a polyaxial or 'multi-planar' embodiment.

Regardless of the differences in pivoting motion, each embodiment the bone anchor assembly generally is configured to provide a spinal fixation system wherein the bone anchor can rotate around its longitudinal or spin axis relative to the receiver sub-assembly (or vice versa) at least prior to a locking the bone anchor assembly with the closure in the final locked position. It will be appreciated that this feature can allow for the rotatable implantation, or screwing in, of the anchor portion of a pre-assembled bone anchor assembly to a desired depth in the bone of a patient without rotation of the receiver sub-assembly, thereby allowing the receiver sub-assembly to be secured by separate tooling, or maintained in a desired alignment, throughout the implantation of the bone anchor. In addition, this feature can allow for the height of the receiver sub-assembly above the bone, or the length of the anchor portion of the bone anchor that is implanted in the bone, to be precisely controlled.

Other than the structural differences between the different embodiments that are either configured to limit the pivoting motion or to allow for greater pivoting motion, it will be further appreciated that the features and aspects of the various embodiments can be substantially the same, and with interchangeability of one or more of the separate components. Thus, a skilled artisan will recognize that a description of certain aspects of the separate components set forth in reference to the mono-planar embodiments of FIGS. 1-62 and 63-64 may also apply to the same aspects of the components illustrated in the multi-planar embodiment of FIGS. 65-69, unless otherwise indicated. Such a spinal fixation system allows for the introduction of a bone anchor having a "universal" capture portion or shank head that is receivable within either of the mono-planar or multi-planar embodiments of the receiver sub-assembly, as further disclosed herein.

Referring now in more detail to the drawing figures, wherein like parts are identified with like reference numerals throughout the several views, FIG. 1 illustrates one embodiment of a mono-planar pivotal bone anchor assembly 10 that includes a bone anchor 20, such as a shank, having a universal shank head or capture portion 22 and an anchor portion 44 opposite the capture portion 22 for securement to or attachment to and within the bone of a patient. The pivotal bone anchor assembly 10 also includes a receiver 50 or housing having a base portion 90 defining an internal cavity or lower portion of a central bore 70 configured to accommodate an articulating retainer sub-assembly 15 coupled to the capture portion 22, and a pair of upright arms 60 defining an open rod channel 56 configured for receiving an elongate rod. The receiver 50 can be initially pivotably secured to the capture portion 22 with a number of separate internal components that have been pre-assembled into the central bore 70 and the rod channel 56 to form a receiver sub-assembly 14. These internal components can include, but are not limited to, the pivoting or articulating retainer sub-assembly 15 that includes a closed ring retainer 100 having a separate open snap ring 120 secured therein (as described in more detail below), and a pressure insert or element 150. After an elongate rod (see FIGS. 61-62) has been positioned within the lower portion of the rod channel 56, a closure 180 can be threadably or otherwise secured into an upper portion of the rod channel 56 to apply pressure to an upper surface of the elongate rod, thereby locking both the elongate rod and the pivotal bone anchor assembly 10 into a final locked position.

As shown in the exploded assembly view of FIG. 1 and isolated views of FIGS. 2-4, the bone anchor 20 has a universal capture portion 22, or universal shank head, at a proximal end 23 that includes one or more frusto-conical outer surfaces 30 that are centered on the bone anchor's longitudinal or spin axis 21, and a body 40 extending distally from the capture portion 22 and having an attachment or anchor portion 44 at a distal end 47 configured for fixation to the bone of a patient. In one aspect the body 40 of the bone anchor can further comprise both the anchor portion 44 as well as a narrower neck portion 22 extending longitudinally between the anchor portion 44 and the universal capture portion 22. Although shown in the figures as a shank body with bone engagement threads 43, it is foreseen that the anchor portion 44 of the body 40 could also be configured as a hook blade to the narrower neck portion 42.

The frusto-conical outer surface 30 can be widest toward the lower end of the universal capture portion 22 (i.e. the end that is closest to the neck 42 or anchor portion 44 of the bone anchor 20), and then can narrow or taper while moving upward toward the upper end 23 and top surface 24 of the capture portion 22. The frusto-conical outer surface 30 can further include a horizontal capture recess 32 extending into and circumferentially around a mid-portion thereof, with the capture recess 32 having a height between an upper step surface 31 and a lower step surface 33. In one aspect the frusto-conical outer surface 30 of the universal capture portion 22 can have a taper angle of about two degrees. In another aspect the taper angle can range from about one degree to about five degrees, or greater. In addition, the outwardly-facing recessed surface 34 of the capture recess 32 that extends between the upper step surface 31 and the lower step surface 33 can also have a similar taper, as shown in the drawings, or can have a different taper, a straight cylindrical profile, or even a curved profile, and the like.

The universal capture portion 22 can further include a lower partial-spherical outer surface 38 that curves downwardly and inwardly from the lower end of the frusto-conical outer surface 30 toward the neck 42 of the body 40 of the bone anchor. In one aspect the lower partial-spherical outer surface 38 can extend radially outward beyond the lower end portion of the frusto-conical outer surface 30 to create an outer lip structure 37 that is further defined, in part, by an upwardly-facing annular ledge 36. The capture portion 22 can further include a top edge surface 28 at the upper end of the frusto-conical outer surface 30 that is chamfered, beveled, or radiused with respect to the frusto-conical outer surface 30 and to a horizontal top surface 24, so as to ease the entry of the proximal end 23 of the bone anchor 20 into the retainer aperture, as described in more detail below. It will also be appreciated that the tapered angle of the frusto-conical outer surface 30 itself can further facilitate the insertion of the capture structure 22 into the retainer aperture, so as to be easier than the insertion provided by a capture structure of a bone anchor having a cylindrical shape with straight sides into a retainer aperture defined by a non-tapered inner surfaces.

As shown in the drawings, the top surface 24 of the capture portion 22 can be an annular planar top surface that surrounds an internal drive feature or drive socket 26. The illustrated internal drive feature 26 is an aperture formed in the top surface 24, and in one aspect can be a multi-lobular or star-shaped aperture, such as those sold under the trademark TORX, or the like, having internal faces 25 designed to receive a multi-lobular or star-shaped tool for rotating and driving the bone anchor 20 into the vertebra. It is foreseen that such an internal tool engagement structure 26 may take a variety of tool-engaging forms and may include one or more apertures of various shapes, such as a pair of spaced apart apertures or a hex shape designed to receive a hex tool (not shown) of an Allen wrench type. The seat or base surface 27 of the drive feature 26 can be disposed perpendicular to the shank axis, with the drive feature otherwise being coaxial with the longitudinal axis 21 of the bone anchor 20. In operation, a driving tool is received in the internal drive feature 26, being seated at the base surface 27 and engaging the internal faces 25 of the drive feature for both driving and rotating the universal capture portion 22 and the anchor portion 44 of the bone anchor into the vertebra, either before or after the bone anchor 20 is attached or coupled to the receiver sub-assembly. If attached, the threaded anchor portion 44 of the body 40 of the bone anchor can be driven into the vertebra with the driving tool extending downward through the central bore 70 of the receiver 50.

In one aspect the bone anchor 20 or shank can be cannulated (and also fenestrated for the application of bone cement) with a narrow bore 46 or aperture extending through the entire length thereof and centered about the longitudinal axis 21 of the shank. The bore 46 can be defined by an inner cylindrical wall with a lower circular opening at the shank tip 48 and an upper circular opening communicating with the internal drive socket 26 at the seat surface 27, and is coaxial with the body 40 and the universal capture portion 22 of the bone anchor 20. The bore 46 provides a passage through the shank interior for a length of wire (not shown) inserted into the vertebra prior to the implantation of anchor portion 44 of the bone anchor 20, the wire providing a guide for insertion of the anchor portion 44 into the vertebra. The bore 46 can also provide for a pin to extend therethrough and beyond the shank tip 48, the pin being associated with a tool to facilitate insertion of the body 40 of the bone anchor into the vertebra.

To provide a biologically active interface with the bone, the body 40 of the bone anchor, including both the threaded anchor portion 44 and the neck 42, may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bioceramic calcium phosphate coatings include, but are not limited to: alpha-tri-calcium phosphate and beta-tri-calcium phosphate (Ca3(PO4)2, tetra-calcium phosphate (Ca4P2O9), amorphous calcium phosphate and hydroxyapatite (Ca10(PO9)6(OH)2). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIGS. 1 and 5-6, a "bone plow" structure or scraper ring 140 can be positioned within an upper portion of the capture recess 32 of the universal capture portion 22 prior to the capture portion 22 being uploaded into the receiver sub-assembly. The scraper ring 140 is configured to have a tight friction fit against the outwardly-facing recessed surface 34 of the horizontal capture recess 32. When the recessed surface 34 is tapered or frusto-conical, as described above, the tight fit of the scraper ring 140 against the tapered recessed surface 34 can serve to keep the scraper ring at the upper end of the horizontal capture recess 32, as shown in FIG. 6.

The scraper ring 140 has a height between a top surface 143 and a bottom surface 145, and a width between an outer surface 144 and an inner surface 146, with the width being sufficiently large for the outer surface 144 of the scraper ring 140 to project radially outward beyond the frusto-conical outer surface 30 of the capture portion 22, so as to be engageable by the snap ring 120 during the upward passage of the universal capture portion 22 through the retainer aperture 110, as described below. This can operate to drive the scraper ring 140 downward toward the lower ledge or step surface 33 of the capture recess 32, thereby scraping and removing or clearing the upper portion of the capture recess of any debris or tissue prior to engagement of the capture recess 32 by the snap ring 120. It is foreseen that the scraper ring can be formed with different cross-sectional shapes, such as square, rectangular, trapezoidal, that the inner surface 146 can be tapered to match the taper of the recessed surface 34 of the capture recess 32, or that the outer surface 144 can be substantially vertical or even upwardly-outwardly tapered to provide a greater surface area for the snap ring to engage, and the like.

Illustrated in FIGS. 1 and 7-10 is the receiver 50 having a generally U-shaped appearance with a partially discontinuous substantially cylindrical inner profile and a partially cylindrical and partially faceted outer profile, although other profiles are contemplated. The receiver 50 has a centerline vertical axis 51, or axis of rotation, that is shown in FIG. 1 as being aligned with the longitudinal axis 21 of the bone anchor 20, such orientation being desirable, but not required during assembly of the receiver sub-assembly 14 with the bone anchor 20. After the receiver 50 is pivotally attached to the universal capture portion 22, either before or after the bone anchor 20 is implanted in a vertebra, the receiver axis 51 is typically disposed at an angle with respect to the shank axis 21 as shown, for example, in FIG. 59.

The receiver 50 generally comprises a base portion 90 defining an internal cavity 83 or lower portion of a generally cylindrical central or axial bore 70 that is centered around the receiver's centerline vertical axis 51, and a pair of upright arms 60 extending upwardly from the base 90 to form the upper portion of the receiver and to define an upwardly-open channel 56 configured for receiving the elongate rod. Each of the upright arms 60 has an interior face 54 that includes a discontinuous upper portion of the central bore 70, which may be bounded on either side by opposing vertical planar end surfaces 57 that curve downwardly into U-shaped lower saddle surfaces 58. In one aspect the opposing end surfaces 57 and saddle surfaces 58 can define the front and back ends of the upwardly open channel 56 that also opens laterally onto a front face 66 and a back face 67 of the receiver 50, respectively. The central bore 70 can extend from top surfaces 52 of the upright arms 60 at the proximal end 53 of the receiver downwardly through both the open channel 56 and the internal cavity 83 to communicate with a bottom surface 98 of the receiver 50 through a bottom opening 94. In addition, it is foreseen that the receiver 50 can be configured to have a closed rod-receiving channel, in which case the top surfaces 52 and upper portions of the upright arms 56 can connect together to form a solid ring surrounding the central bore 70.

The upper or channel portion of the central bore 70 further includes a discontinuous guide and advancement structure 72 formed into the interior faces 54 of the upright arms 60, which guide and advancement structure 72 is configured to engage with a complementary structure formed into the outer side surfaces of the closure 180, as described more fully below. The guide and advancement structure 72 in the illustrated embodiment is a discontinuous helically wound flangeform having a square-shaped thread 73. It will be understood, however, that the guide and advancement structure 72 could alternatively comprise an interlocking thread, a buttress thread, a modified buttress thread, a reverse angle thread, or other thread-like or non-thread-like helically wound advancement structure for operably guiding and advancing the closure 180 downward between the arms 56 under rotation, as well as for torqueing against when the closure 180 abuts against the elongate rod. Additionally, the various structures and surfaces forming the guide and advancement structure 72 can also be configured to resist, to inhibit, to limit, or to preferentially control the splay of the upright arms 60 while advancing the closure 180 downward between the upright arms 60 under the rotation and when torqueing against the elongate rod to generate a downwardly-directed pressure that locks the bone anchor assembly into position.

Moving downward along the interior faces 54 of the upright arms 60, the portion of the central bore 70 located between the vertical end surfaces 57 can include a runout groove 74 immediately below the guide and advancement structure 70 that is followed, in turn, by a discontinuous upper cylindrical ledge structure 76 and a discontinuous inner recess 78 defined by a downward-facing upper arcuate surface 77 and an upward-facing lower arcuate surface 79. A partially discontinuous lower cylindrical surface 80 can then extend from the inner recess 78 downwardly and around the central bore 70 below the lower saddle surfaces 58 to form an inner sidewall surface that defines an upper portion of the internal cavity 83 of the receiver 50.

As shown in the drawings, the internal cavity 83 further includes a lower seating surface 84 extending downwardly and inwardly from the ledge surface 82 to proximate the bottom opening 94. In one aspect the lower seating surface 84 can be a partial-spherical seating surface that is slidably mateable with a rounded outer surface of the closed ring retainer 100 and, at high angles of articulation of the bone anchor 20 with respect to the receiver 50, with the lower partial-spherical outer surface 38 of the universal capture portion 22. Nevertheless, it is foreseen that the other shapes or structures for the lower seating surface of the central bore, which are also slidably mateable with the rounded outer surface of the closed ring retainer 100 and/or the lower partial-spherical outer surface 38 of the bone anchor 20, are also possible, including but not limited to a non-spherical surface, a conical surface, a chamfered surface, a sharp edged or stepped structure, and the like, and are considered to fall within the scope of the present disclosure.

As discussed in more detail below, the pivotal bone anchor assemblies of the present disclosure can be configured for either rotatable and mono-planar pivotal motion (FIGS. 1-64) or rotatable or multi-planar pivotal motion (FIGS. 65-69) between the receiver sub-assembly and the universal bone anchor 20 or shank. For the embodiment of the receiver 50 illustrated in FIGS. 7-10, which is configured for mono-planar motion, the inwardly-extending lower seating surface 84 generally comprises a non-continuous circumferential partial spherical seating surface proximate the bottom opening 94 with opposed vertically-aligned recesses or pockets 86 formed therein. The opposed vertical pockets 86 can be sized and shaped for receiving opposing rounded (or otherwise shaped) protrusions or pegs projecting outwardly from the mono-planar embodiment of the closed ring retainer 100 when the mono-planar retainer sub-assembly 15 is installed into the receiver, thereby limiting the pivoting motion of the closed ring retainer to the single plane defined by a pivot axis extending between the pegs, as discussed below.

In one aspect the opposed vertical pockets 86 are formed into the cylindrical sidewall 80 of the central bore 70 that defines an upper portion of the cavity 83, and extend downwardly through the lower ledge 82 and into an upper portion of the seating surface 84, leaving a lower portion of the seating surface 84 untouched and extending continuously 360 degrees around the central bore 70 between the lower ends of the opposed vertical pockets 86 and a lower edge that can define, together with a lowermost cylindrical or chamfered surface 95, the bottom opening 94 of the receiver 50. The opposed vertical pockets 86 can further include curvilinear bottom surfaces 87 of the pockets having an axis of curvature that is aligned with the geometric center of the lower seating surface 84. As described in more detail below, the curvilinear bottom surfaces 87 of the pockets 86 can be configured to slidably engage with the bottom surfaces of the opposing rounded protrusions or pegs of the closed ring retainer 100, so that the opposing rounded pegs rotate on the curvilinear bottom surfaces 87 of the pockets 86 at the same time that the rounded outer surface of the closed ring retainer slides across of the lower seating surface 84 of the receiver cavity 83. In embodiments where the lower seating surface is inwardly and downwardly curved, such as that shown in the drawings, the opposed vertical pockets 86 can become deeper toward their lower ends, thereby providing the pockets with wider curvilinear bottom surfaces 87.

As noted above, the receiver 50 can have a partially cylindrical and partially faceted outer profile. In the illustrated embodiment, for example, the partially cylindrical portions can include curvate side outer surfaces 62 of the upright arms 60 opposite the interior faces 54 that extend downward from the top surfaces 52 of the upright arms toward a lower tapered surface 96 of the base 90 that angles inwardly to the bottom surface 98 of the receiver 50. The receiver 50 can further include upper curvate-extending instrument engaging grooves 64 below the top surfaces 52 of the upright arms 56 that extend horizontally across the curvate side outer surfaces 62 to the front face 66 and the back face 67 of the receiver 50.

Likewise shown in the drawings, the faceted or planar portions of the receiver 50 may comprise front and back outer planar faces 92 on the receiver base 90 below the open channel 56, and which can extend upwardly as narrow flats 68 on the front and back faces 66, 67 of the upright arms. The faceted or planar portions of the receiver 50 can further include side outer planar faces (not shown) and/or tool receiving and engaging recesses (also not shown) formed into the curvate side outer surfaces 62 below the upper instrument engaging grooves 64, and which can be oriented perpendicular to the front and back outer planar faces 92. In one aspect the upper instrument engaging grooves 64, the front and back outer planar faces 92, the flats 68, and any other planar tool-engagement surface or recess can serve together as outer tool engagement surfaces that allow for tooling to more securely engage and hold the receiver 50 during an initial pre-assembly with the internal components to form the receiver sub-assembly 14, during coupling of the receiver sub-assembly to the bone anchor 20, either after or before the implantation of the body 40 of the bone anchor into a vertebra, and also during further assembly of the receiver sub-assembly 14 with the elongate rod and the closure 180.

Furthermore, it will be appreciated that the receiver 50 can include additional features and aspects not shown in the drawings, including but not limited to inwardly-threaded breakoff extensions extending upwardly from the tops of the upright arms for interfacing with tooling and for guiding the elongate rod and the outwardly-threaded closure into the receiver channel. It is also foreseen that other shapes and configurations for the interior and exterior surfaces of the receiver 50, different from those shown in the drawings while providing for similar interaction and functionality of the various components of the pivotal bone anchor assembly, are also possible and considered to fall within the scope of the present disclosure.

Illustrated in FIGS. 1 and 11-14 is the mono-planar embodiment of the closed ring retainer 100 comprising a continuous O-ring body 102 having a rounded outer surface, such as partial spherical outer surface 104, extending between annular top edge 103 and bottom edge 117 surfaces, respectively, and having opposing outwardly-projecting rounded pegs 106. The O-ring body 102 further includes a retainer aperture 110 defined by a tapered inner surface 112 that can be configured to loosely slidably engage with the frusto-conical outer surface 30 of the universal capture portion 22 of the bone anchor 20, and a retainer aperture recess 114 which extends into and circumferentially around a mid-portion of the tapered inner surface 112. In one aspect the retainer aperture recess 114 can be defined by an upper annular surface 113, a lower annular surface 115, and an inner sidewall surface 116.

As described in more detail below, the mono-planar closed ring retainer 100 is securable within the cavity 83 of the receiver 50 with the opposing rounded pegs 106 positioned within the vertically-aligned opposing pockets 86 or recesses, with the partial spherical outer surface 104 of the O-ring body 102 being frictionally engaged with the lower seating surface 84, and with the retainer aperture 110 being centered above the bottom opening 94 of the receiver 50. When the opposing rounded pegs 106 are positioned within the opposed vertical pockets 86, the pivoting motion of the closed ring retainer 100 relative to the receiver is limited the single plane defined by a pivot axis extending between the pegs 106.

Additionally, the partial-spherical outer surface 104 of the closed ring retainer 100 can have the same radius as the lower partial-spherical surface outer surface 38 of the universal capture portion 22, in which case the partial-spherical surfaces 104, 38 may align with each other to form a substantially spherical capture head when the bone anchor 20 is coupled to the closed ring retainer 100. In this configuration the bottom edge surface 117 of the O-ring body 102 can be adjacent, or even contacting, the upwardly-facing annular ledge surface 36 of the universal capture portion 22 (described above) when the bone anchor 20 is coupled to the closed ring retainer 100 (as shown in FIGS. 51-54).

With the reference to FIGS. 1 and 15-17, the pivotal bone anchor assembly 10 further includes an open snap ring 120 having a slit or slot 128 that allows for expansion of the snap ring 120 during assembly of the bone anchor 20 to the receiver sub-assembly 14. The snap ring 120 has a height between a top surface 123 and a bottom surface 125 and a width between an outer side surface 124 and an inner surface 126, and further defines a snap ring aperture 127 that is smaller than the retainer aperture 110 of the closed ring retainer 100 when the snap ring 120 in a neutral or free state (i.e. neither compressed nor expended).

Figure 18:
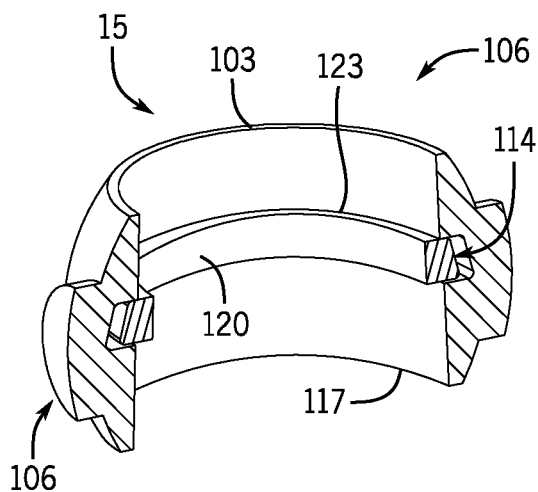
FIG. 18 is a cross-sectional perspective view of the closed ring retainer of FIG. 11 and the snap ring of FIG. 15 after assembly together into a retainer sub-assembly.
Figure 19:
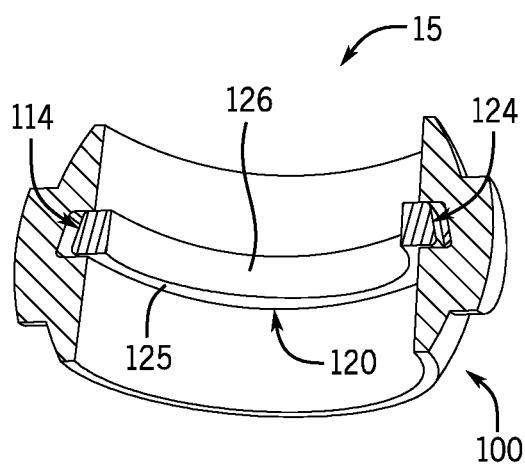
FIG. 19 is another cross-sectional perspective view of the retainer sub-assembly of FIG. 18.
Figure 20:
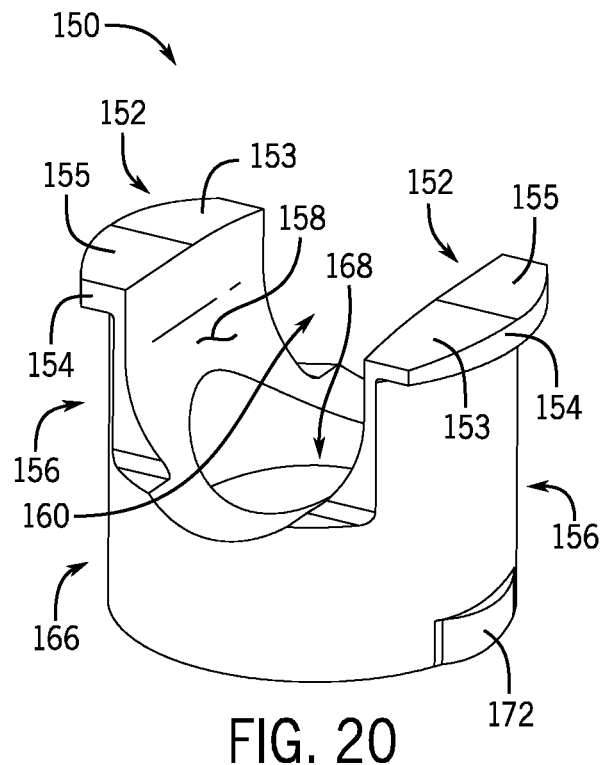
FIG. 20 is a top perspective view of the pressure insert of the pivotal bone anchor assembly of FIG. 1.
Figure 21:
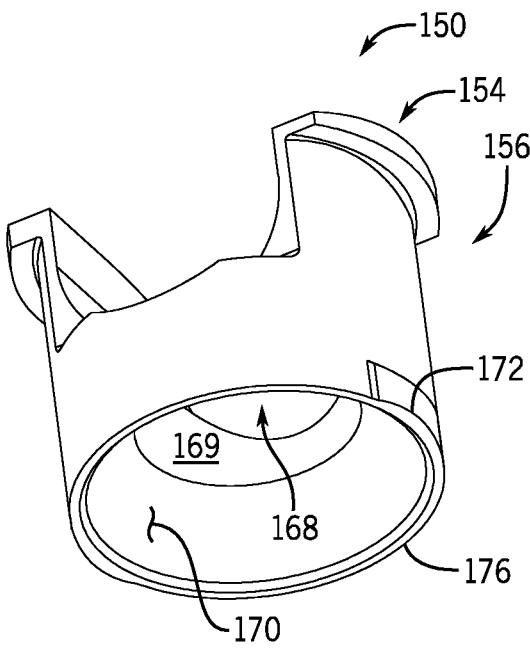
FIG. 21 is a bottom perspective view of the pressure insert of FIG. 20.
Figure 22:
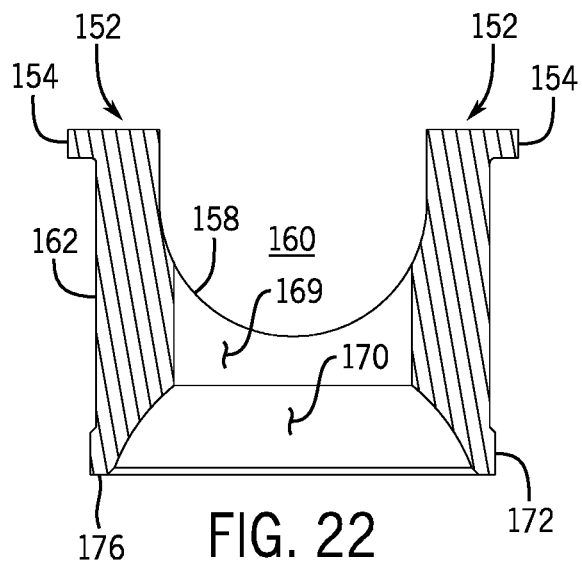
FIG. 22 is a cross-sectional side view of the pressure insert of FIG. 20.
Figure 23:
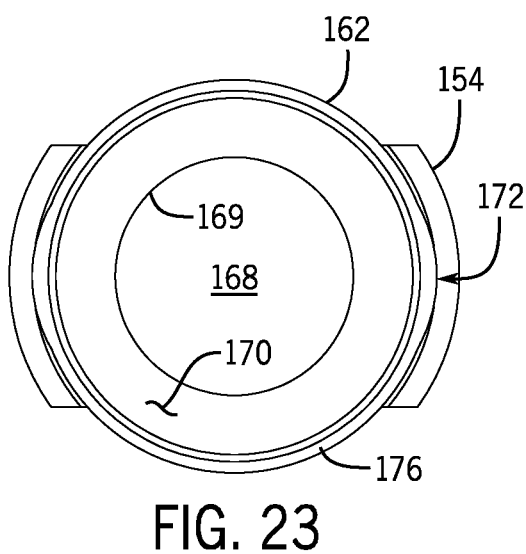
FIG. 23 is a bottom view of the pressure insert of FIG. 20.
Figure 24:
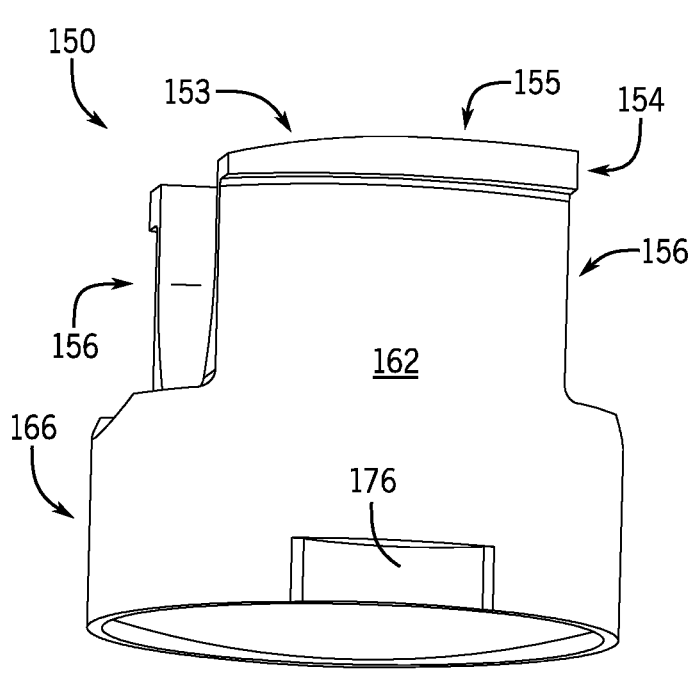
FIG. 24 is a side perspective view of the pressure insert of FIG. 20.
Figure 25:
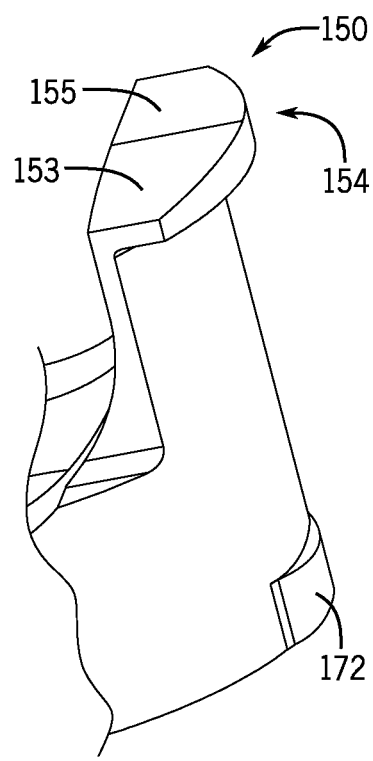
FIG. 25 is a sectioned side perspective view of the pressure insert of FIG. 20

As shown in FIGS. 18-19, the snap ring 120 can be positioned within the retainer aperture recess 114 of the closed ring retainer 100 to form the retainer sub-assembly 15, with the snap ring 120 in its neutral or free state projecting partially into the retainer aperture 110 of the closed ring retainer 100, and having a space or gap between the outer side surface 124 of the snap ring and the inner sidewall surface 116 of the retainer aperture recess 114 that allows for the expansion of the snap ring 120 within the retainer aperture recess 114. Although the retainer aperture recess 114 is shown as a generally cylindrically-shaped annular recess and the snap ring is shown as having a generally cylindrically-shaped cross-section, and as being freely movable within the recess 114, it is foreseen that the snap ring and/or retainer aperture recess can include additional structures useful for stabilizing and centralizing the snap ring within the retainer aperture recess, or can be of different size or shape. In addition, it is further foreseen that other embodiments of the ring retainer may include one or more slots, and therefore may not be completely closed. Nevertheless, a non-closed embodiment of the ring retainer need not be expandable.

With the reference to FIGS. 1 and 20-23, the pivotal bone anchor assembly 10 further includes a pressure insert 150 that is configured to transfer a downwardly directed force from the elongate rod and closure 180 to the closed ring retainer 100, thereby locking the pivotal bone anchor assembly 10. Accordingly, the pressure insert 150 includes an inner upward-facing rod-seating surface 158 that is engageable with the elongate rod, and a rounded (as shown) or tapered lower surface 170 that is engageable with the rounded outer surface 104 of the closed ring retainer 100. In one aspect the inner upward-facing surface 158 can be a curved saddle surface that extends between two upright insert arms 156 that are formed integral with a lower base portion 166, with the insert base 166 having a cylindrical outer surface 162 sized to be slidably received within the central bore 70 of the receiver 50. In another aspect, the concave lower surface 170 of the pressure insert can be a partial spherical surface that extends upward and inward from an annular lower bottom edge 176 to define a downwardly-opening concave surface. As described in more detail below, in some embodiments of the pivotal bone anchor assembly 10 the rounded lower surface 170 of the pressure insert is also engageable with the top edge surface 28 of the universal capture portion 22 as it projects upwardly above the top edge surface 103 of the closed ring retainer 100. The pressure insert further includes a central tool-receiving aperture 168 defined by an inner cylindrical surface 169 configured to slidably receive a drive tool (not shown) that extends downwardly through the central bore 70 to engage the internal drive socket 26 formed into the top end 23 of the universal shank head 22.

The pressure insert 150 positioned within the central bore 70 of the receiver 50 may be further configured so as to apply a continuous downward pressure onto the closed ring retainer 100 prior to the assembly of the elongate rod and closure 180, such as in a shipping state configuration, and thereby provide a frictional engagement between the closed ring retainer 100 and the receiver lower seating surface 84 that prevents the closed ring retainer from moving, pivoting, or rotating within the central bore 70 of the receiver 50 both prior to and during the universal capture portion 22 being uploaded into the receiver sub-assembly 14. In this design one or more exterior surfaces of the pressure insert 150 may be releasably engaged with one or more interior surfaces of the central bore 70 of the receiver 50 to apply the downward pressure to the closed ring retainer 100. As shown in the drawings, the exterior surfaces of the pressure insert 150 can be upward-facing surfaces such as, for example, the top surfaces 153, 155 of flanges 154 that project radially outward from the top portions of the insert upright arms 156. Correspondingly, the one or more interior surfaces of the central bore can be downward-facing surfaces such as, for example, the downward-facing upper arcuate surfaces 77 of the discontinuous recess 78 formed into the central bore 70. As describe above in reference to FIGS. 7-10, the discontinuous recess 78 can be located above the lower seating surface 84 in the receiver cavity 83 and below the discontinuous guide and advancement structure 72 formed into the interior faces 54 of the receiver arms 56. The engagement between the insert 150 and the receiver 50 can further be described as overlapping and biasing.

Furthermore, the exterior upward-facing exterior surfaces of the pressure insert can be engaged with the downward-facing interior surfaces of the receiver central bore of the receiver using any one of a number of different designs or configurations. In the representative embodiment of the pivotal bone anchor assembly shown in FIGS. 20-23 and 33-41, for example, the pressure insert 150 can be rotatable with a tool, in some embodiments up to through about a 90 degree range (approximately ¼ turn) around the centerline vertical axis 51 of the receiver 50, with the upward-facing surfaces (e.g. the top surfaces 153, 155 of flanges 154) entering into releasable frictional engagement with the downward-facing surfaces (e.g. downward-facing upper arcuate surface 77 of the discontinuous recess 78) so as to apply the downward pressure to the closed ring retainer 100. Moreover, in one aspect the upward-facing surfaces of the insert 150 can further include ramped surfaces 153 that provide a camming action that converts the rotary motion of the pressure insert 150 into a linear downward movement that generates the initial downward pressure onto the closed ring retainer 100, prior to installation of the rod and the locking of the assembly 10 by the closure 180.

The pressure insert 150 may additionally include an indexing structure configured to releasably engage with a complementary indexing structure formed into the central bore 70 of the receiver 50, upon rotation of the pressure insert about the receiver centerline vertical axis 51, so as to inhibit further rotation of the pressure insert out of its rotated position. For example, and as shown in FIGS. 20-22 and 39-40, in one embodiment the indexing structure of the insert can comprise opposed outwardly projecting nubs or protuberances 172 located near the lower bottom edge 176 of the base 166 of the insert that releasably engage with the opposed vertical pockets 86 formed into the central bore 70 of the receiver 50 upon rotation of the pressure insert 150 into its rotated position. It is foreseen that other structures can be used to hold the insert relative to the receiver, such as crimps or separate rings, to inhibit rotational and/or translational movement of the insert about the vertical axis of the receiver.

Figure 26:
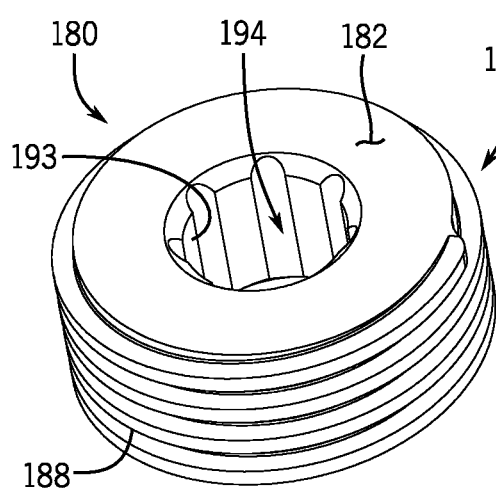
FIG. 26 is a top perspective view of the closure of the pivotal bone anchor assembly of FIG. 1.
Figure 27:
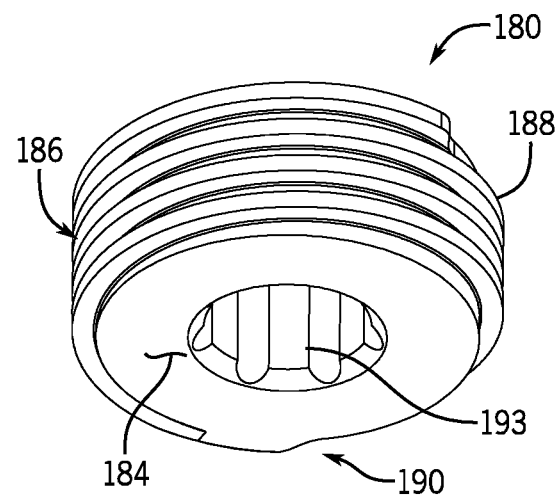
FIG. 27 is a bottom perspective view of the closure of FIG. 26.

With reference to FIGS. 26-27, the closure 180 of the pivotal bone anchor assembly 10 can comprise a substantially cylindrical closure body having a guide and advancement structure 188 formed into its outer surface 186, and which continuous guide and advancement structure is mateable with the complementary discontinuous guide and advancement structure 72 formed into the upper portion of the central bore 70 that is defined by the interior faces 54 of the receiver upright arms 60. The closure 180 can also include one or more drive structures 194, such as a central drive socket and/or a breakoff head, formed into or attached to the top surface 182 of the closure body. The continuous guide and advancement structure 188 of the closure can further include one or more start structures 190 that are specifically shaped to engage one or more lead-in structures of the discontinuous guide and advancement structure 72 of the receiver 50 in a controlled fashion.

Figure 28:
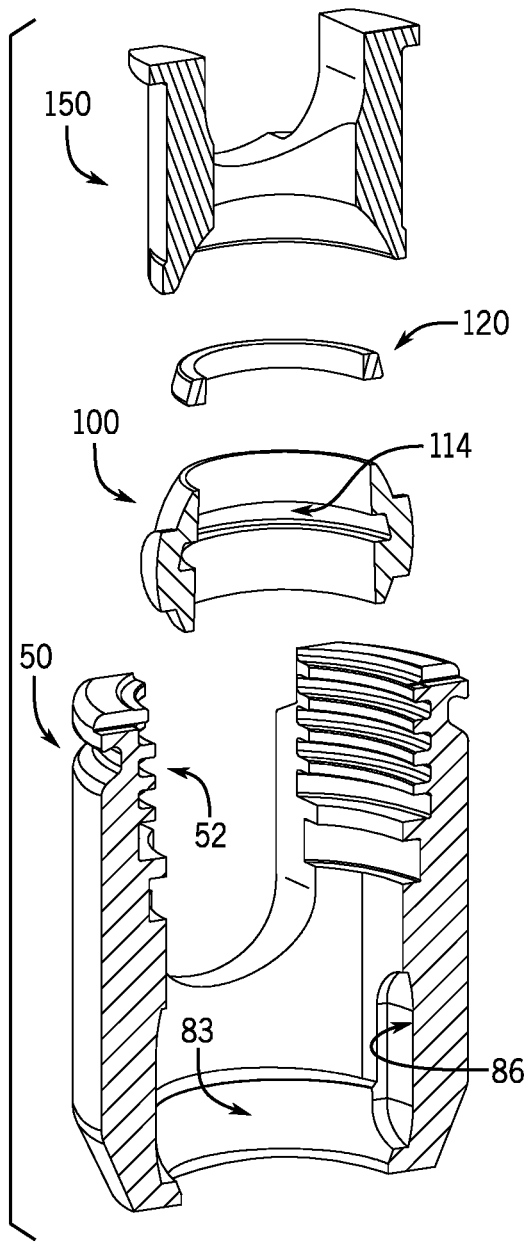
FIG. 28 is an exploded side view of the components of a receiver sub-assembly prior to their pre-assembly into a shipping configuration.

Illustrated in FIG. 28 are the individual components of the mono-planar pivotal bone anchor assembly 10 that, in many embodiments, can be pre-assembled together into a receiver sub-assembly at a factory or manufacturing facility, prior to shipping to a hospital or surgery center and engagement with the universal capture portion 22 of the bone anchor 20 in the surgical setting. As described above, these components generally include the receiver 50, the retainer sub-assembly 15 that includes the closed ring retainer 100 with the separate open snap ring 120 secured therein, and the pressure insert 150. In one aspect the pre-assembled components being assembled into a receiver sub-assembly can be further defined as the shipping state position. It will be appreciated, however, that in other embodiments the shipping state can include the further assembly of the receiver sub-assembly together with the bone anchor 20 at the factory or manufacturing facility. It will also be appreciated that in yet other embodiments the individual components described above can also be pre-assembled into the receiver sub-assembly at the hospital or surgery center prior to implantation in a patient.

Figure 29:
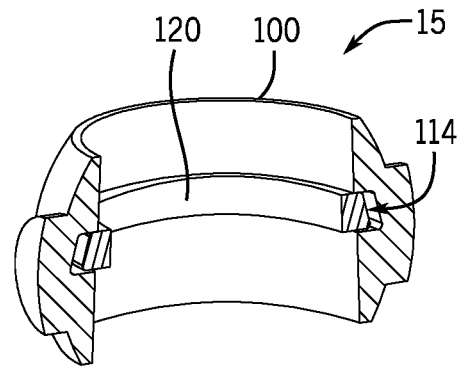
FIG. 29 is a cross-sectional perspective view of the closed ring retainer and snap ring of FIG. 28 after assembly together into a retainer sub-assembly.
Figure 30:
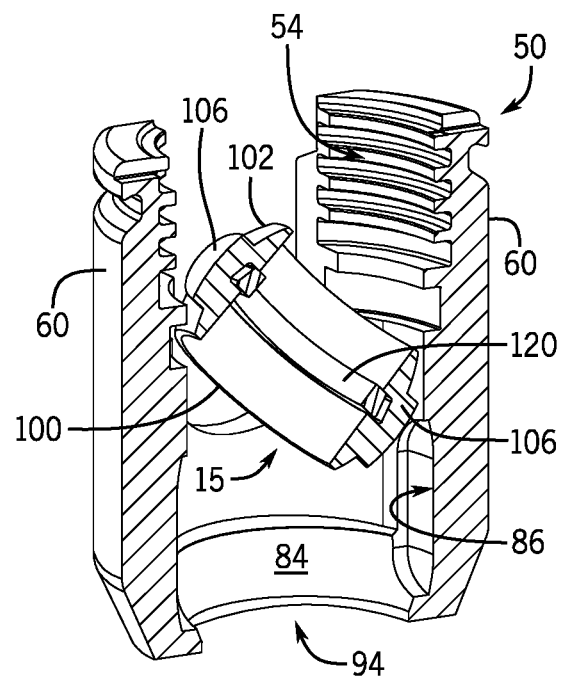
FIG. 30 is a partially cut-away front perspective view of the receiver of FIG. 28 with the retainer sub-assembly being installed therein.
Figure 31:
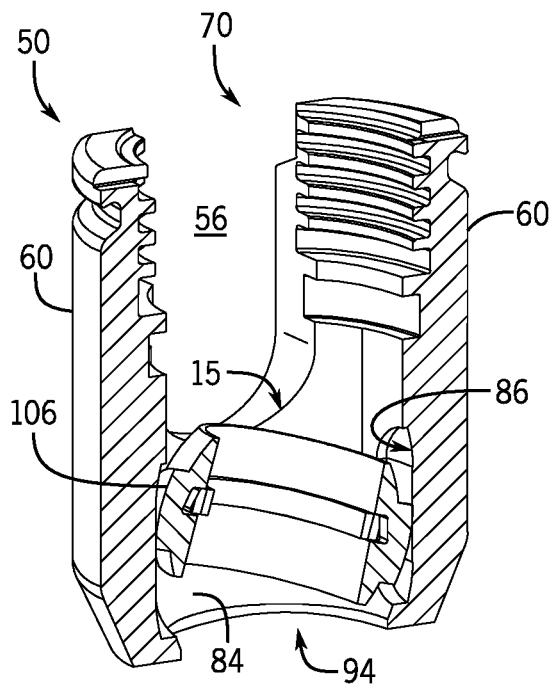
FIG. 31 is another partially cut-away front perspective view of the receiver with the retainer sub-assembly being installed therein.
Figure 32:
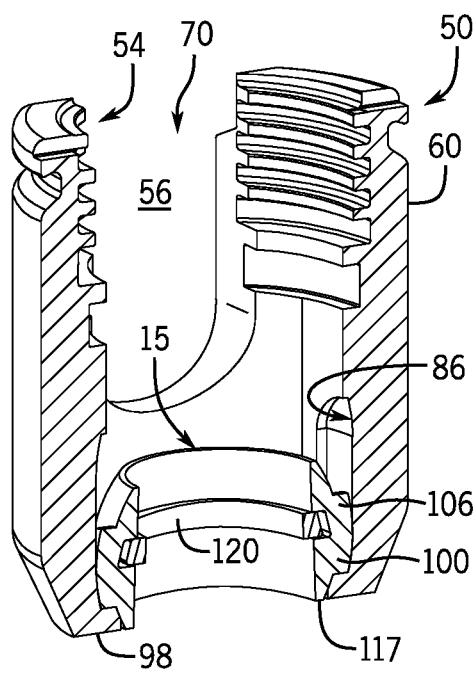
FIG. 32 is a partially cut-away front perspective view of the receiver with the retainer sub-assembly installed and seated therein.

To begin the pre-assembly of the receiver sub-assembly, the snap ring 120 can first be installed into the retainer aperture recess 114 of the closed ring retainer 100 (FIG. 29) to form the retainer sub-assembly 15, as described above. The retainer sub-assembly 15 can then be top-loaded into the receiver 50, as shown in FIGS. 30-32. This can be achieved, for instance, by rotating the closed ring retainer 100 to a substantially vertical position so that the top and bottom surfaces of the closed ring retainer 100 face the interior faces 54 of the receiver arms 60, downloading the closed ring retainer 100 through the receiver channel 56 and into the receiver cavity 83 or lower portion of the central bore 70, and then rotating the closed ring retainer 100 back downward until the rounded outer surface 104 of the closed ring retainer rests on the inwardly-extending lower seating surface 84 of the receiver cavity 83. With the mono-planar embodiment shown in FIGS. 28-32, the closed ring retainer 100 can be positioned so that the opposing rounded pegs 106 projecting outwardly from the O-ring body 102 are aligned to enter into the vertically-aligned opposing pockets 86 formed into the central bore 70, so as to allow the closed ring retainer 100 to rotate completely back downward to the horizontal position. Alternatively, it is foreseen that in other embodiments the snap ring 120 may be installed into the closed ring retainer 100 after the positioning of the closed ring retainer within cavity 120 of the receiver 50.

With the closed ring retainer 100 in the horizontal position resting on the inwardly-extending lower seating surface 84 of the receiver cavity 83, the retainer aperture 110 of the closed ring retainer can be centered within the bottom opening 94 of the receiver 50 and aligned with the vertical axis of the receiver 51. Moreover, the bottom edge surface 117 of the closed ring retainer 100 can also be substantially flush with the bottom surface 98 of the receiver 50, or even somewhat recessed.

As described above, when the opposing rounded pegs 106 of the retainer 100 are positioned within the opposed vertical pockets 86 of the receiver 50, the pivoting motion of the closed ring retainer 100 relative to the receiver 50 is limited the single plane defined by the pivot axis extending between the pegs 106. Because the opposed vertical pockets 86 are aligned with the interior faces 54 of the receiver arms 56 that define the rod receiving channel 56, as shown in the drawings, the mono-planar pivoting motion of the retainer 100 can thus be limited to the sagittal plane. It will nevertheless be appreciated that the location of the opposed vertical pockets 86 may be adjusted in either direction within the receiver cavity 83 so that the mono-planar pivoting motion of the retainer 100 is limited to the medial-lateral plane, or to any plane of pivoting motion located between the sagittal and medial-lateral planes.

Figure 33:
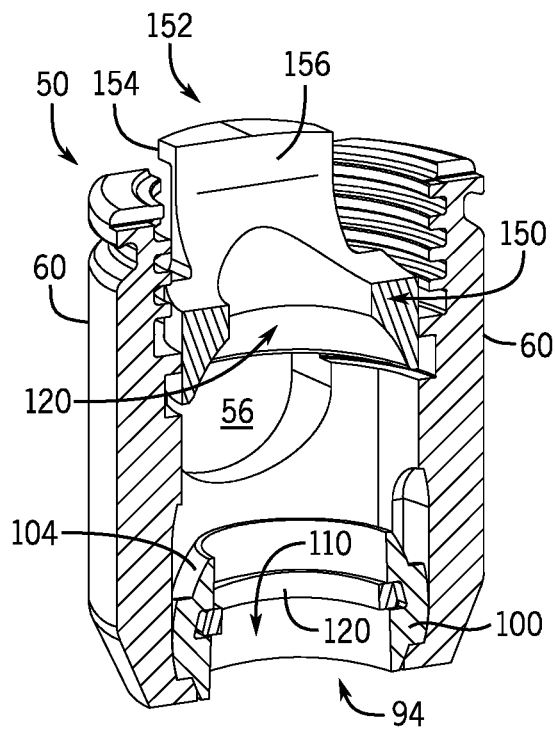
FIG. 33 is a partially cut-away front perspective view of the receiver with the seated retainer sub-assembly, with the pressure insert now being installed therein.
Figure 34:
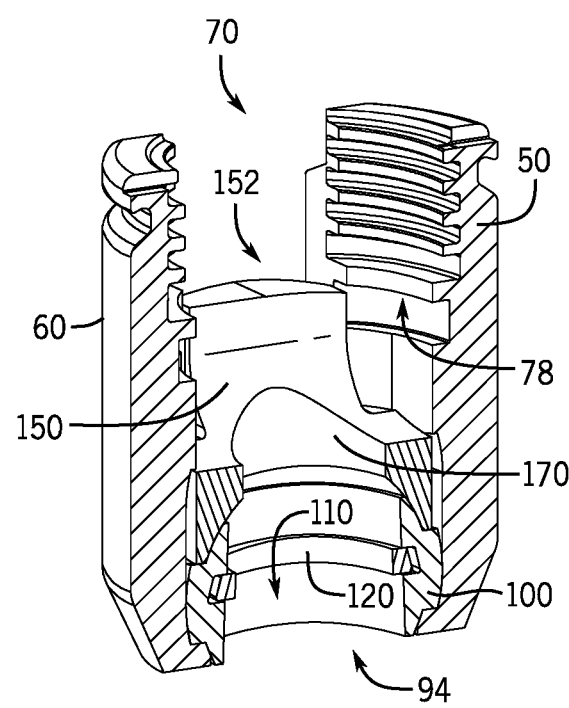
FIG. 34 is another partially cut-away front perspective view of the receiver with the seated retainer sub-assembly and the pressure insert being installed therein.
Figure 35:
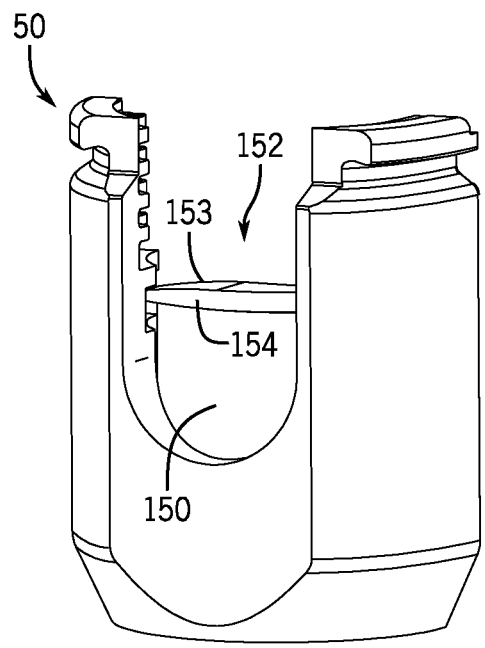
FIG. 35 is back perspective view of the receiver with the seated retainer sub-assembly and the pressure insert being rotated therein.
Figure 36:
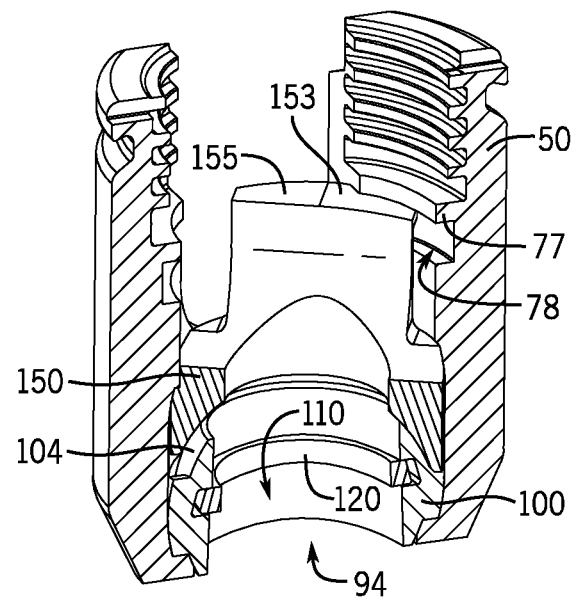
FIG. 36 is a partially cut-away front perspective view of the receiver with the seated retainer sub-assembly and the pressure insert of FIG. 35.
Figure 37:
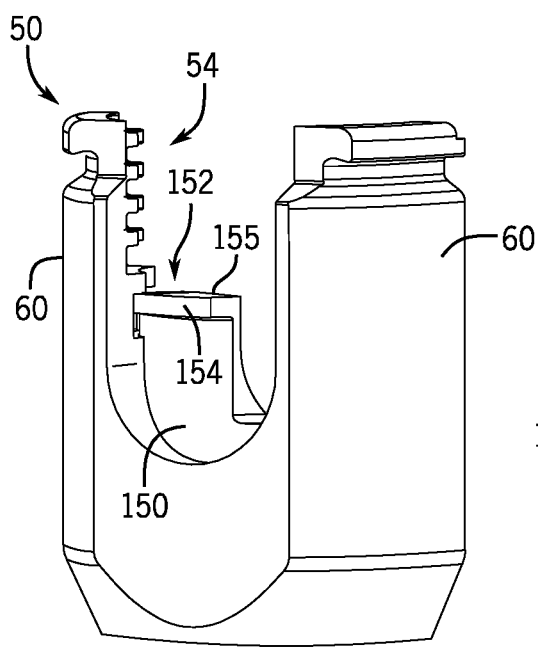
FIG. 37 is another back perspective view of the receiver with the seated retainer sub-assembly, with the pressure insert being further rotated therein.
Figure 38:
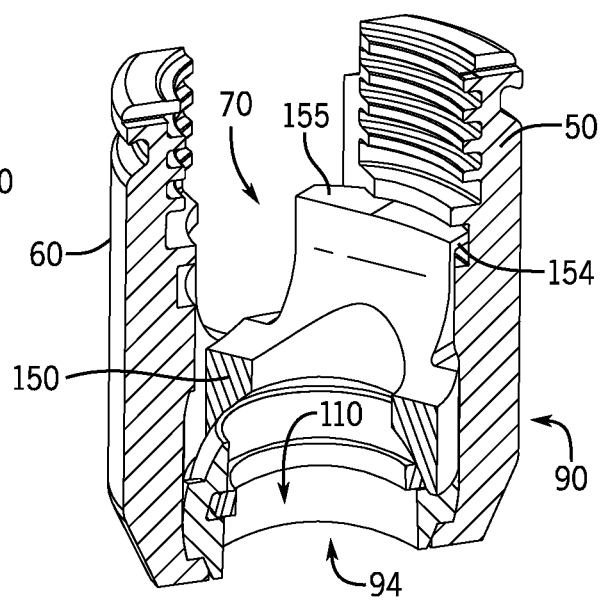
FIG. 38 is a partially cut-away front perspective view of the receiver with the seated retainer sub-assembly and the pressure insert of FIG. 37.

After the closed ring retainer 100 is seated on the inwardly-extending lower seating surface 84 of the receiver 50, the pressure insert 150 may then be top-loaded into the central bore 70 so as to frictionally secure and firmly hold the closed ring retainer 100 into the shipping state position, with the retainer aperture 110 of the closed ring retainer 100 being co-aligned with the bottom opening 94 of the receiver 50. As shown in FIGS. 33-34, this can be achieved by positioning the pressure insert 150 above the central bore 70 of the receiver with the insert arms 156 and radially projecting flanges 154 being aligned with the receiver channel 56, and then downloading the pressure insert 150 into the receiver channel 56 until the flanges 154 reach the level of the discontinuous inner recess 78 formed into the central bore 70 for this type of twist-in-place insert. At the same time the concave lower surface 170 and the annular bottom edge 176 of the pressure insert 150 can become engaged with the upper portion of the rounded outer surface 104 and the upper portions of the opposing rounded pegs 106, respectively, of the closed ring retainer 100.

As shown in FIGS. 35-38. the pressure insert 150 may then be rotated around its longitudinal axis (which is co-linear with the centerline vertical axis 51 of the receiver 50) so that the radially projecting flanges 154 enter into the discontinuous inner recess 78, with the upward-facing top surfaces of the flanges 152 slidably engaging with the downward-facing upper arcuate surfaces 77 of the inner recess 78. This can serve to prevent the pressure insert 150 from moving back up within the central bore 70 after it has been rotated into its rotated position, and thereby maintain the pivotable closed ring retainer 100 within the central bore 70 below the insert 150.

In embodiments where the upward-facing top surfaces 152 of the flanges 154 also include a ramped section 153 and a straight section 154, the rotation of the radially projecting flanges 154 into the inner recess 78 can thereby provide a camming action that creates a downward pressure onto the closed ring retainer 100 to further frictionally secure the closed ring retainer 100 within the central bore 70 in the shipping state position. The concave lower surface 170 of the pressure insert 150 is thus frictionally engaged with the rounded outer surface 104 of the closed ring retainer 100 that is, in turn, further frictionally engaged with the seating surface 84 of the receiver cavity 83. These frictional engagements on the upper and lower surfaces of the mono-planar closed ring retainer 100 can clamp the retainer in place to prevent inadvertent pivoting of the retainer about the rounded pegs 106 during shipping and handling, and thereby maintain the retainer aperture 110 of the retainer 100 centered and aligned with the bottom opening 94 of the receiver 90.

Figure 39:
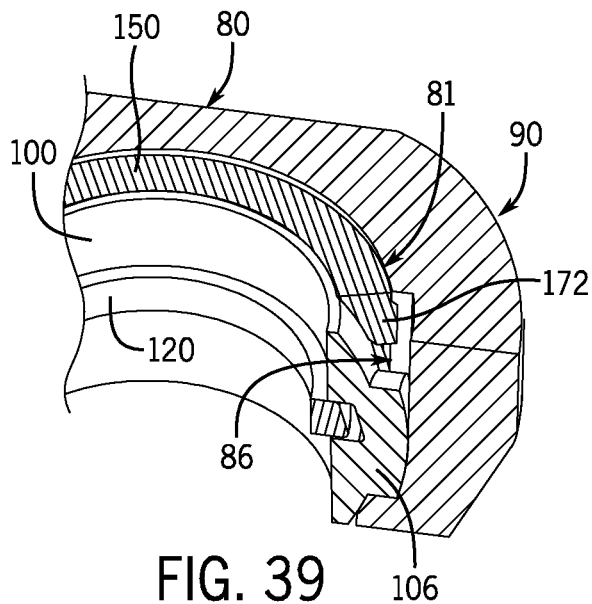
FIG. 39 is a close-up cut-away perspective view of the receiver with the seated retainer sub-assembly, with the pressure insert being rotated therein.
Figure 40:
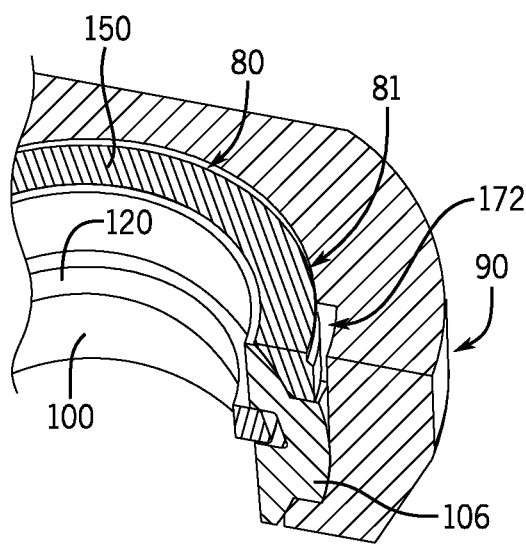
FIG. 40 is another close-up cut-away perspective view of the receiver with the seated retainer sub-assembly, with the pressure insert being fully rotated therein.

Furthermore, in embodiments where the cylindrical outer surface 162 of the pressure insert 150 includes the opposed outwardly projecting nubs or protuberances 172, during rotation of the pressure insert 150 about its longitudinal axis the projecting nubs 172 can slidably frictionally engage the inner sidewall surface 80 of the central bore 70 or receiver cavity 83 at the base 90 of the receiver, as shown in FIG. 39, until the projecting nubs 172 slide or snap into the opposed vertical pockets 86 above the rounded pegs 106 of the closed ring retainer 100, as shown in FIG. 40, after which the projecting nubs can inhibit further rotation the pressure insert 150, either forward or backward, out of its rotated position.

To facilitate this engagement, in one aspect the inner sidewall surface 80 of the receiver cavity 83 may not be round or truly cylindrical, but instead may be slightly oblong, with the slightly longer axis aligned with the rod channel 56 of the receiver and the slightly shorter axis aligned with the opposed vertical pockets 86 to created slightly 'flattened' zones 81 laterally adjacent the pockets 86. This can allow the projecting nubs 172 to freely enter the receiver cavity 83 during downloading of the pressure insert 150 that is aligned with the receiver channel 56, but then to become increasingly frictionally engaged with the inner sidewall surfaces 80 during rotation of the pressure insert 150 into alignment with the upright arms 60, as the projecting nubs 172 slide or scrape across the flattened zones 81, until the nubs 172 finally snap into the vertical pockets 86 upon the pressure insert 150 reaching its rotated position. Again, other structures for holding the insert 150 in alignment with the central bore 70 are also possible and considered to fall within the scope of the present disclosure, including a reversal of the male/female relationship with an inwardly-protruding projection being formed on an inner surface of the central bore and a recess or notch being formed into the outer surface of the pressure insert.

Figure 41:
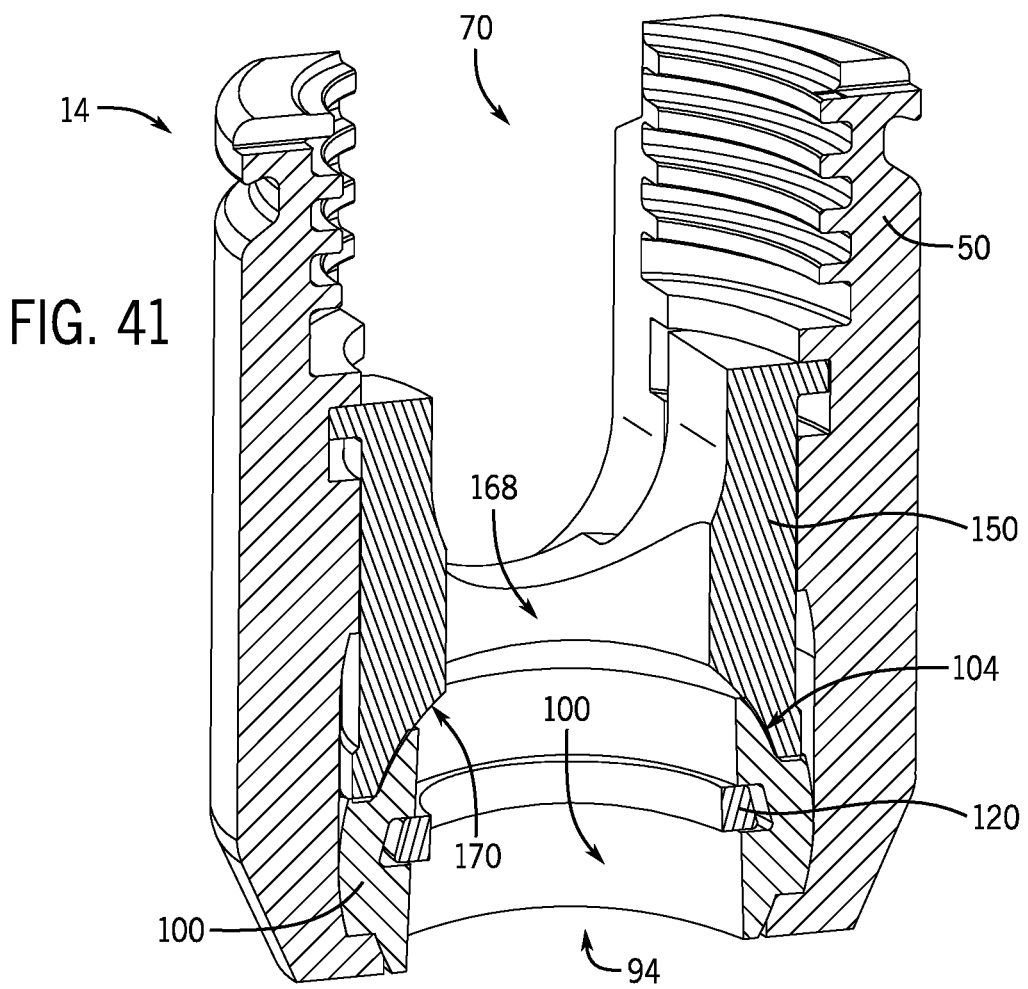
FIG. 41 is a partially cut-away front perspective view of the receiver with the seated retainer sub-assembly and the pressure insert being fully rotated therein to form a pre-assembled receiver sub-assembly in the shipping state.

The pressure insert 150 is now secured within the central bore 70 of the receiver 50 in its rotated position, as shown in FIG. 41, with the concave lower surface 170 of the pressure insert engaging the rounded outer surface 104 of the closed ring retainer 100 so as to apply a downward pressure that, in turn, frictionally clamps and secures the closed ring retainer (and enclosed snap ring 120) within the central bore 70 against pivotal motion. In addition, the engagement between the annular bottom edge 176 and/or projecting nubs 172 of the pressure insert 150 with the upper portion of the cylindrical base 108 of the opposing rounded pegs 106, as noted above, also serves to hold the pegs 106 down against the curvilinear bottom surfaces 87 of the vertical pockets 86, and thereby restrain the closed ring retainer 100 from lifting or twisting up out of the pockets 86 under out-of-plane loading on the receiver sub-assembly 14. Accordingly, the pre-assembly of the receiver sub-assembly 14 is now complete, and the receiver sub-assembly 14 is ready for storage and/or shipping and handling, and for eventually attachment to the universal capture portion 22 of a bone anchor 20 or shank either prior to or during spinal surgery.

Furthermore, and as described below in additional embodiments of the disclosure, it is foreseen that other structures and interconnections between the components of the receiver sub-assembly 14 can be used to secure the closed ring retainer in its pre-assembled position within the receiver cavity portion 83 with its retainer aperture aligned and centered with the bottom opening 94 at the base 90 of the receiver 50, and are considered to fall within the scope of the present disclosure.

One representative embodiment for assembling the receiver sub-assembly 14 to the universal capture portion 22 of the bone anchor 20 is illustrated in FIGS. 42-57. For instance, and with initial reference to FIG. 42, the receiver sub-assembly 14 can be first positioned above the proximal end 23 of the bone anchor 20, with the retainer aperture 110 of the closed ring retainer 100, that is centered within bottom opening 94 of the receiver 50, being generally aligned with the frusto-conical outer surface 30 of the universal capture portion 22. As shown in the drawings, the universal capture portion 22 can optionally include the scraper ring 140 positioned within the upper portion of the capture recess 32 prior to the capture portion 22 being uploaded into the receiver sub-assembly 14.

Figures 42, 43:
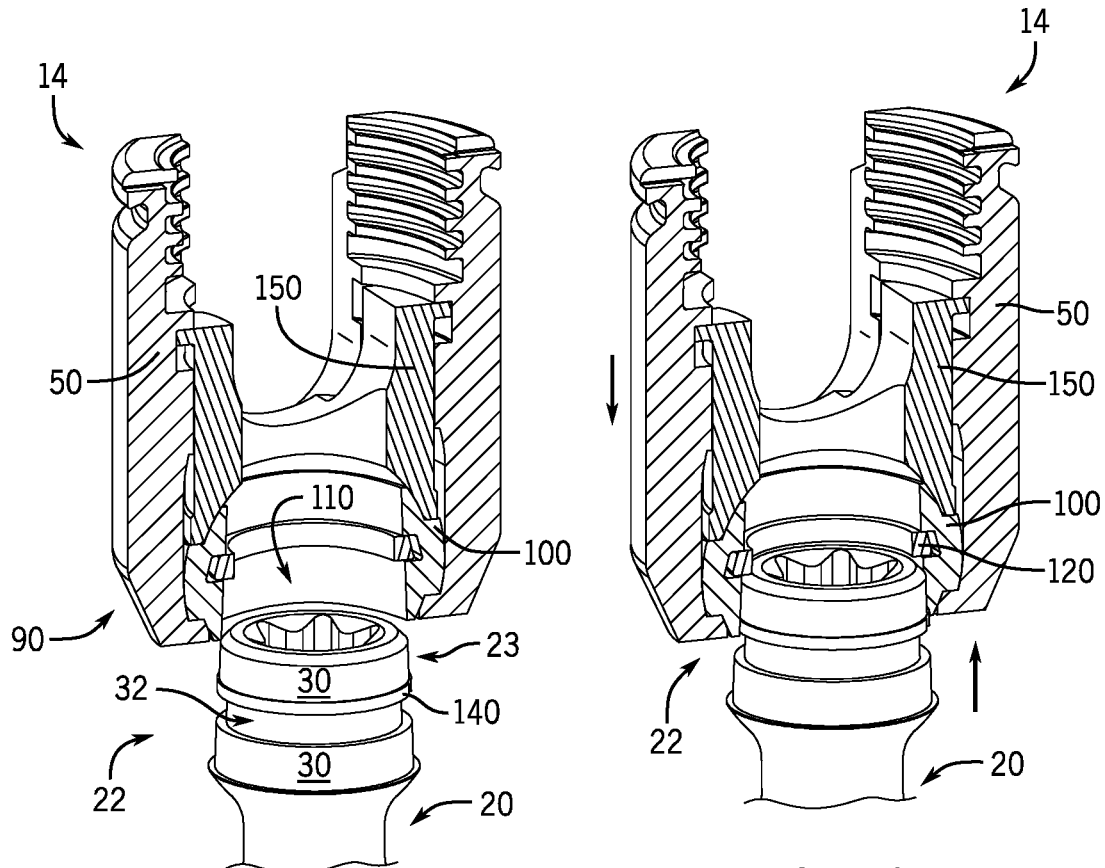
FIG. 42 is a partially cut-away front perspective view of the receiver sub-assembly positioned above the universal capture portion of a bone anchor.
FIG. 43 is a partially cut-away front perspective view of the receiver sub-assembly moving downward onto the universal capture portion of the bone anchor.
Figure 44:
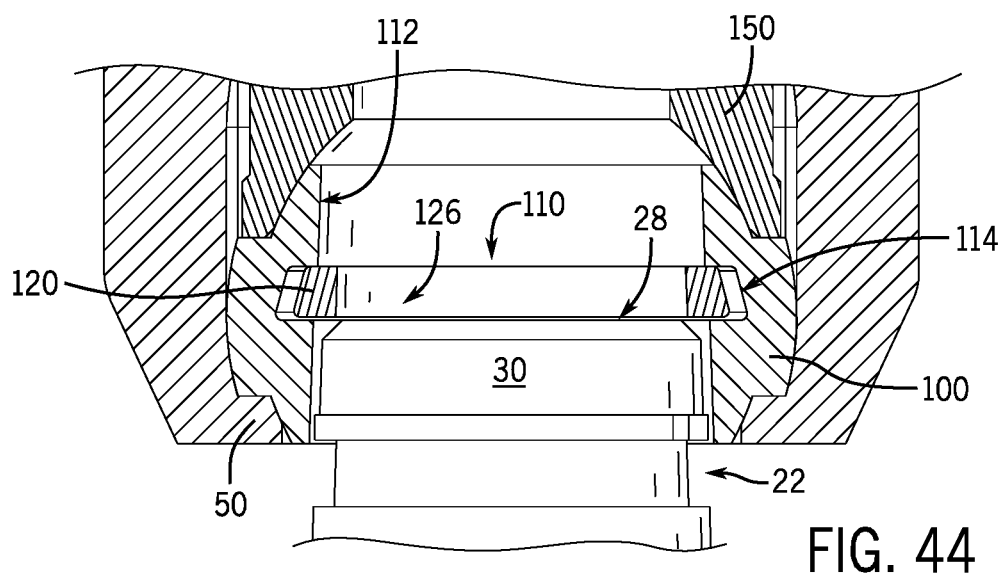
FIG. 44 is a close-up cross-sectional side view of the receiver sub-assembly and universal capture portion of FIG. 43.

With reference to FIGS. 43-44, the receiver sub-assembly 14 is then dropped downward (or the bone anchor 20 is moved upward, depending on the frame of reference of the reader) until the top edge or top edge surface 28 of the universal capture portion 22 enters the retainer aperture 110 and travels upward through the closed ring retainer 100 toward the snap ring 120. As previously described, the top edge of the universal capture portion 22 can be formed with a chamfered or beveled (or alternatively with a radius) surface 28, so as to facilitate slidable engagement with the tapered inner surface 112 upon entry of the upper end 23 of the universal capture portion 22 into the retainer aperture 110.

Figure 45:
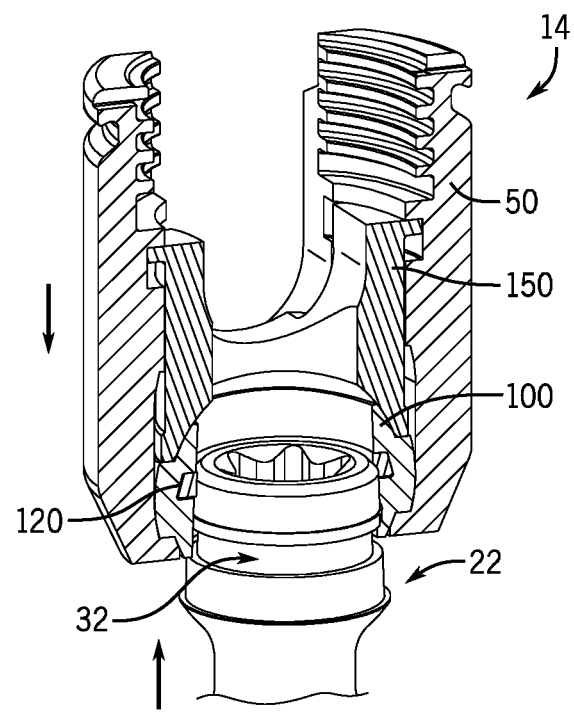
FIG. 45 is a partially cut-away front perspective view of the receiver sub-assembly moving downward until the universal capture portion of the bone anchor engages the snap ring enclosed within the closed ring retainer.
Figure 46:
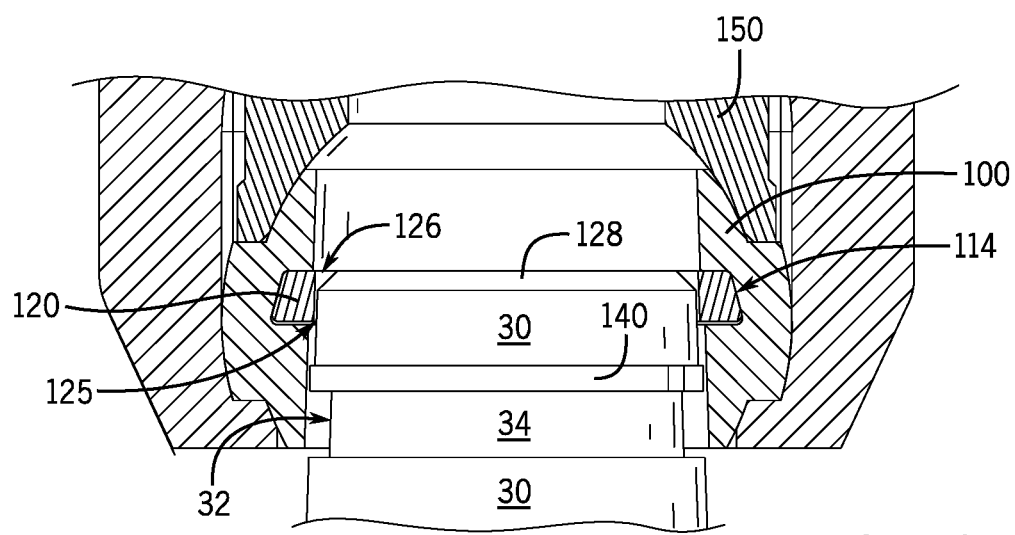
FIG. 46 is a close-up cross-sectional side view of the receiver sub-assembly and universal capture portion of FIG. 45.

With reference to FIGS. 45-46, the receiver sub-assembly 14 continues to move downward (or the bone anchor 20 moves upward) until the top edge surface 28 of the universal capture portion 22 enters the aperture 127 of the open snap ring 120 that is secured within retainer aperture recess 114 of the closed ring retainer 100. With engagement of the inner surface 126 of the snap ring aperture 127 first by the chamfered top edge surface 28 of the universal capture portion 22 and then by the upper portion of the frusto-conical outer surface 30, the snap ring 120 is gradually forced to expand outwardly into the retainer aperture recess 114 of the closed ring retainer 100, while the closed ring retainer itself maintains its original dimensions and does not expand outwardly. It will thus be appreciated that the expansion space for the snap ring, which performs the expansion/contraction/connection (i.e. retaining device) function of the retainer sub-assembly 15, is now provided within the closed ring retainer itself. Accordingly, the cavity portion 83 of the central bore 70 of the receiver 50 does not require an expansion chamber portion to provide space for the expansion of the retaining device during the uploaded of the universal capture portion 22 into the receiver sub-assembly 14, as may be present in pivotal bone anchor assemblies of different design.

Figure 47:
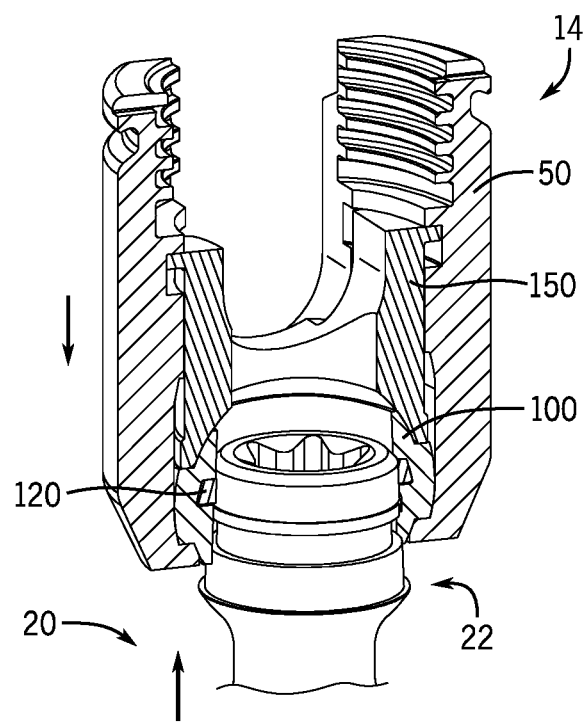
FIG. 47 is a partially cut-away front perspective view of the receiver sub-assembly moving downward as the snap ring approaches the scraper ring secured within the horizontal capture recess of the universal capture portion of the bone anchor.
Figure 48:
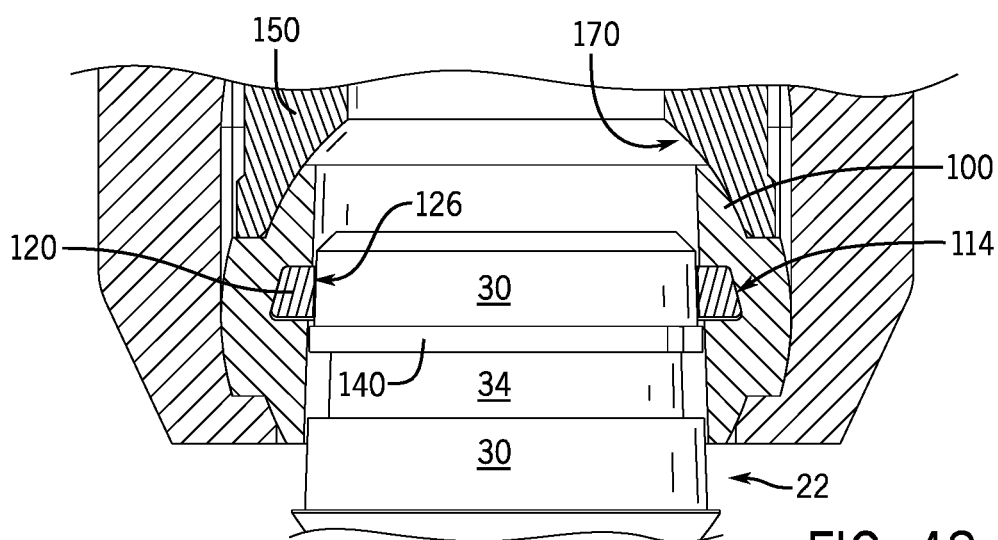
FIG. 48 is a close-up cross-sectional side view of the receiver sub-assembly and universal capture portion of FIG. 47.

With reference to FIGS. 47-48, the receiver sub-assembly 14 continues to move downward (or the bone anchor 20 moves upward) as the inner surface 126 of the snap ring aperture slides downwardly along the upper portion of the frusto-conical outer surface 30, while the snap ring 120 approaches the horizontal capture recess 32 of the universal shank head 22. The tapered shape of the frusto-conical outer surface 30 causes the snap ring 120 to continue to expand as it moves downwardly toward the capture recess 32.

Figure 49:
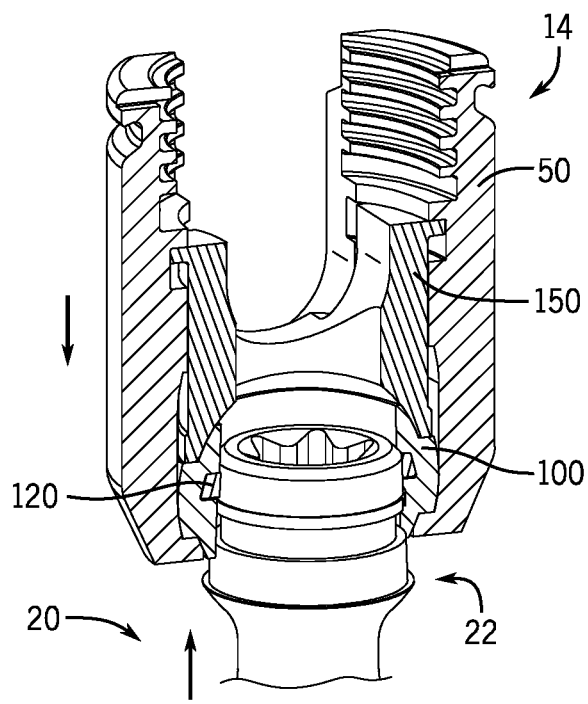
FIG. 49 is a partially cut-away front perspective view of the receiver sub-assembly moving downward as the snap ring engages the scraper ring secured within the horizontal capture recess of the universal capture portion of the bone anchor.
Figure 50:
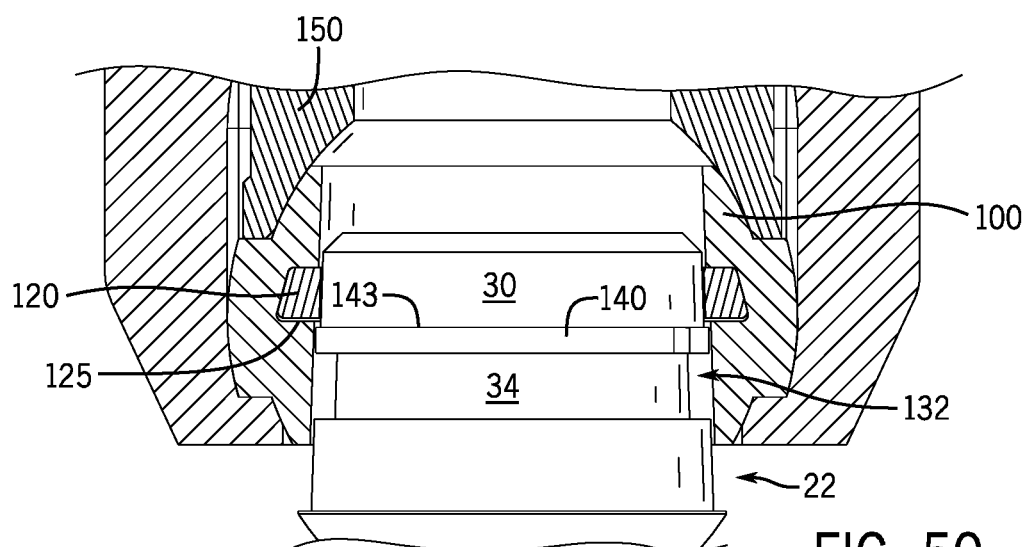
FIG. 50 is a close-up cross-sectional side view of the receiver sub-assembly and universal capture portion of FIG. 49.

With reference to FIGS. 49-50, the snap ring 120 eventually reaches the horizontal capture recess 32 and the scraper ring 140, if used, that is secured therein, with the bottom surface 125 of the snap ring 120 engaging the top surface 143 of the scraper ring 140 to drive the scraper ring downward toward a lower portion of the capture recess 32. As described above, the scraper ring 140 can have a tight friction fit against the outwardly-facing recessed surface 34 of the horizontal capture recess 32, so that its downward motion can thereby scrape or clear the upper portion of the recessed surface 34 of any debris or tissue prior to engagement of the upper portion of the capture recess 32 by the snap ring 120.

Figure 51:
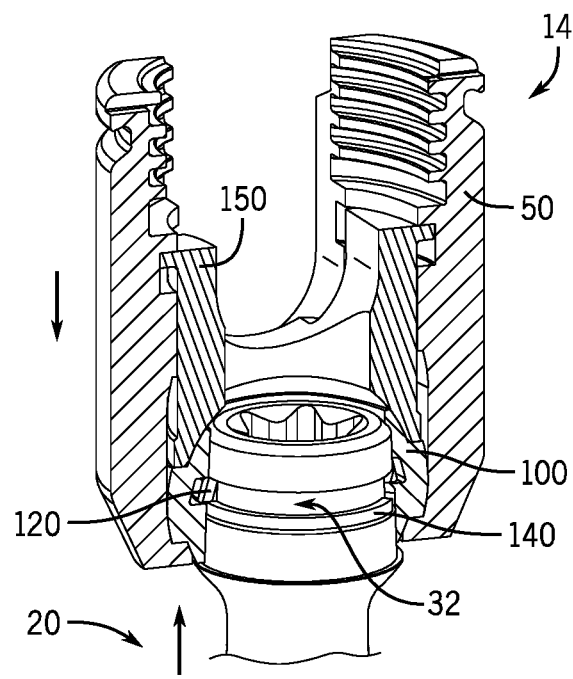
FIG. 51 is a partially cut-away front perspective view of the receiver sub-assembly moving downward as the snap ring snaps into the horizontal capture recess of the universal capture portion of the bone anchor to couple the universal capture portion to the closed ring retainer.
Figure 52:
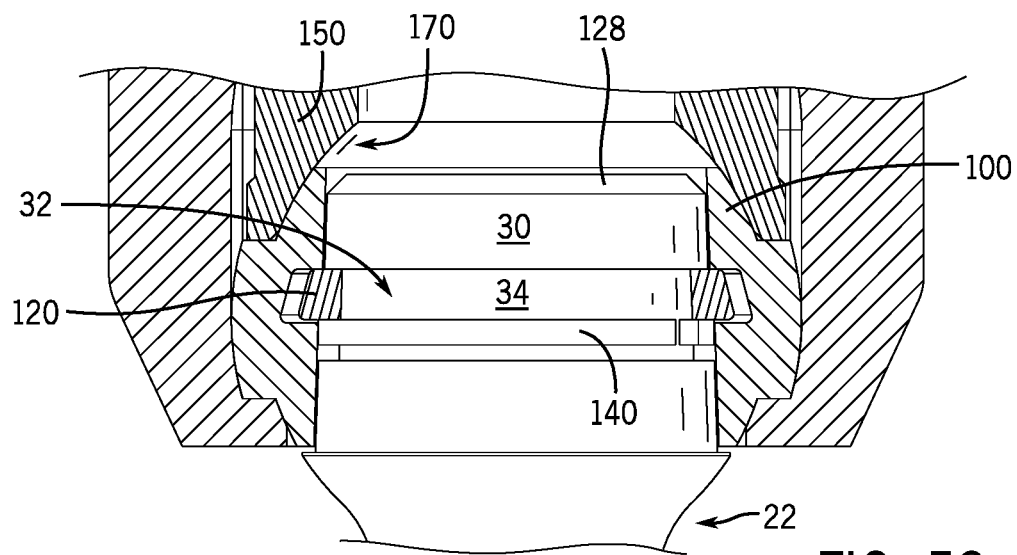
FIG. 52 is a close-up cross-sectional side view of the receiver sub-assembly and universal capture portion of FIG. 51.

With reference to FIGS. 51-52, the receiver sub-assembly 14 continues to move downward (or the bone anchor 20 moves upward) until the snap ring 120 passes beyond the upper portion of the frusto-conical outer surface 30 and snaps into the horizontal capture recess 32, thereby coupling the universal capture portion 22 directly to the closed ring retainer 100, and through the closed ring retainer 100 to the receiver sub-assembly 14. As shown in the drawings, it will be appreciated that the height of the capture recess 32 can be substantially larger than the height of the snap ring 120, in one aspect to allow for manufacturing tolerances between the two features and thereby ensure that the snap ring 120 has sufficient space to snap cleanly into the capture recess 32. In addition, the extra space in the lower portion of the capture recess 32, below the scraper ring 140, can provide a storage space for receiving and holding any debris or tissue that was cleared away by the scraper ring 140 during its downward movement.

Figure 53:
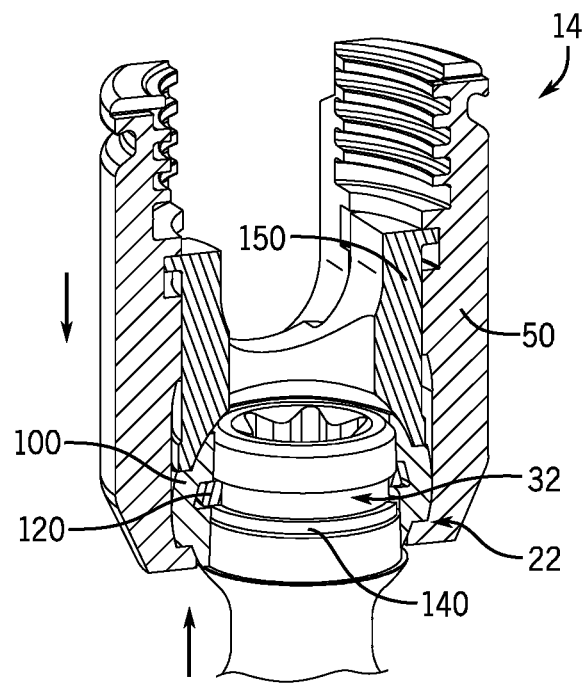
FIG. 53 is a partially cut-away front perspective view of the receiver sub-assembly moving downward until the bottom edge surface of the closed ring retainer abuts the upwardly-facing annular ledge of the universal capture portion.
Figure 54:
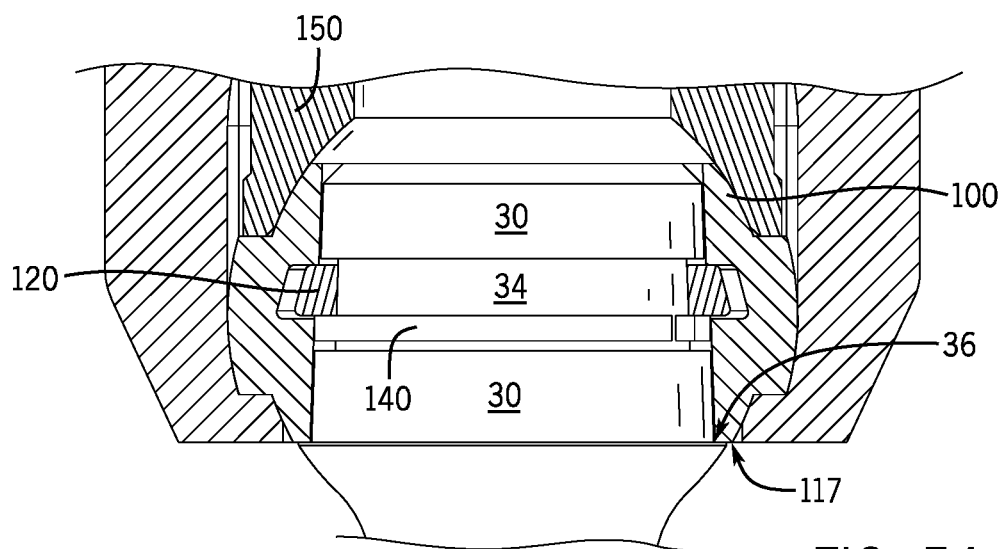
FIG. 54 is a close-up cross-sectional side view of the receiver sub-assembly and universal capture portion of FIG. 53.

With reference to FIGS. 53-54, the receiver sub-assembly 14 continues to move downward (or the bone anchor 20 moves upward) until the bottom edge surface 117 of the closed ring retainer 100 abuts the upwardly-facing annular ledge 36 of the outer lip structure 37 that extends radially outward from the lower end of the frusto-conical outer surface 30. The ledge surface 36 can serve as a stop that prevents the closed ring retainer 100, and hence the entire receiver sub-assembly 14, from traveling too far down the frusto-conical surface 30 during its assembly with the universal capture portion 22. Similarly, the ledge surface 36 can also inhibit excess downward movement when a downwardly-directed force is applied to the receiver sub-assembly 14 after the coupling with the bone anchor 22 such as when, for example, the closure 180 is threadably driven into the guide and advancement structure 72 formed into the upright arm 60 so as to secure the elongate rod within the receiver channel 56.

Figure 55:
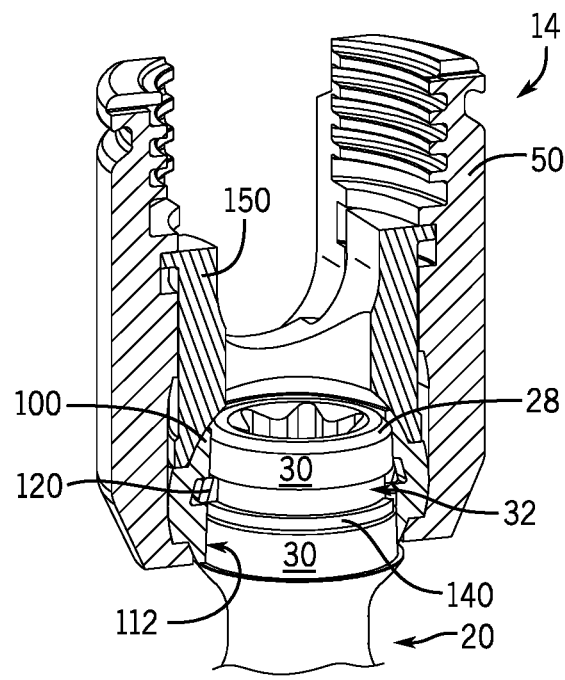
FIG. 55 is a partially cut-away front perspective view of the receiver sub-assembly coupled to the universal capture portion of the bone anchor.

As illustrated in FIG. 55, the receiver sub-assembly 14 is now coupled to the universal capture portion 22 by the snap ring 120 that is secured within both the horizontal capture recess 32 of the capture portion and the retainer aperture recess 114 of the closed ring retainer 100. In one aspect the average outer diameter of the frusto-conical outer surface 30 can be less or slightly less than the average inner diameter of the tapered inner surface 112 that defines the retainer aperture 110, even when the bone anchor is in its most "upward" position (see FIG. 56). This can result in the frusto-conical outer surface 30 being either slightly spaced from or lightly engaged with the tapered inner surface 112, with no significant frictional or press-fit engagement is established between the two tapered surfaces.

Figure 56:
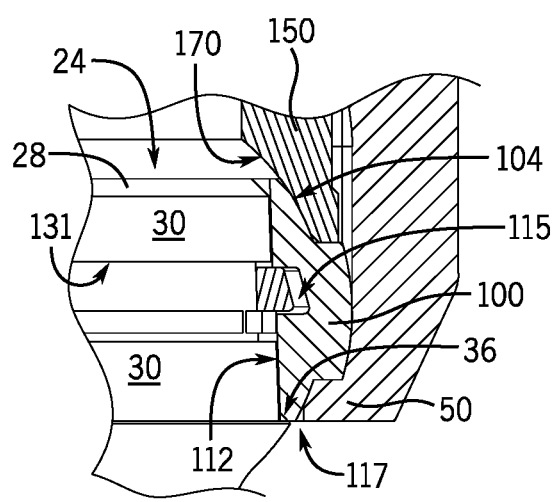
FIG. 56 is a close-up cross-sectional side view of the receiver sub-assembly and universal capture portion of FIG. 55 with the bone anchor is in its most "upward" position.

In this configuration the universal capture structure 22 can be secured to the receiver sub-assembly 14 by the snap ring 120 only, and therefore able to travel vertically within a small range defined by abutting engagements between closed ring retainer 100, the snap ring 120, and the universal shank head 20. As shown in FIG. 56, for example, the upwardly-facing annular ledge 36 of the universal capture portion 22 can abut the bottom edge 117 of the closed ring retainer 100 to define the most "upward" position of the bone anchor 20 relative to the receiver sub-assembly 14. At the other end of the short range of travel illustrated in FIG. 57, the top surface 123 of the snap ring 120 can abut the downward-facing upper shelf 31 of the capture recess 31 simultaneous with bottom surface 125 of the snap ring 120 abutting the upward-facing lower shelf 115 of the retainer aperture recess 114, to define the most "downward" position of the bone anchor 20 relative to the receiver sub-assembly 14.

Moreover, since the frusto-conical outer surface 30 of the universal capture portion 22 may be either slightly spaced from or only lightly engaged with the tapered inner surface 12 of the closed ring retainer 100, as noted above, it will be understood that regardless of the pivotal or angular mobility of the closed ring retainer 100 relative to the receiver 50, the lack of a strong frictional engagement between the frusto-conical outer surface 30 and the tapered inner surface 112 can allow for the universal capture portion 22 to remain freely or frictionally rotatable within the closed ring retainer 100, at least prior to downloading the elongate rod into the receiver channel and locking the assembly with the closure, as discussed below. As noted above, this can allow for the rotatable implantation, or screwing in, of the anchor portion 20 of a pre-assembled bone anchor assembly 10 to a desired depth in the bone of a patient without rotation of the receiver sub-assembly 14, thereby allowing the receiver sub-assembly to be secured by separate tooling, or maintained in a desired alignment, throughout the procedure.

As previously described, the frictional engagement between the closed ring retainer 100 and the receiver lower seating surface 84, due to the downward pressure created by the pressure insert 150 being rotating into position within the central bore 70, can be sufficient to frictionally secure the closed ring retainer into the shipping state position with the retainer aperture 110 of the retainer 100 co-aligned with the bottom opening 94 of the receiver 50, prior to coupling with the bone anchor 20. After coupling the retainer sub-assembly 15 with the universal capture structure 22, however, this same frictional engagement may be insufficient to altogether inhibit any pivoting motion of the combined retainer sub-assembly 15 and bone anchor relative to the receiver 50 by manual manipulation, due to the leverage provided by the downwardly-extending body 40 of the bone anchor 20. Thus, once coupled together and prior to downloading the elongate rod into the receiver channel 56 and locking the assembly with the closure, the closed ring retainer 100 and bone anchor 20 can be pivotably frictionally secured to the receiver 50 with a non-floppy friction fit at the interface between the rounded outer surface 104 of the retainer and the lower seating surface 84 of the receiver cavity.

Figure 57:
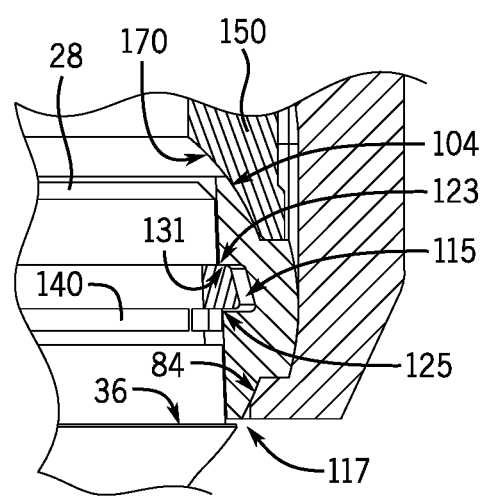
FIG. 57 is a close-up cross-sectional side view of the receiver sub-assembly and universal capture portion of FIG. 55 with the bone anchor is in its most "downward" position.

As shown in FIGS. 55-57, in one aspect the annular top surface 24 and top edge surface 28 of the universal capture portion 22 may be well spaced from the concave lower surface 170 of the pressure insert 150 upon the coupling of the bone anchor 20 with the closed ring retainer 100, so as to create a large gap 132 between the two surfaces 28, 170 that prevents them from coming into contact during the final locking of the bone anchor assembly. In this configuration of the universal capture portion, the concave lower surface 170 of the pressure insert can engage with and apply pressure to the rounded outer surface 104 of the retainer without also directly applying pressure to the universal bone anchor 20, and thereby establish a single load path 133 in final locking that extends downward from the elongate rod through the pressure insert 150 and closed ring retainer 100 to the seating surface 84 and base 90 of the receiver 50.

It will be further appreciated that the force or load applied to the top of the elongate rod by the closure 180 during final locking, and which is subsequently transferred downward through the pressure insert 150 and other components of the receiver sub-assembly to the seating surface 84 and base 90 of the receiver 50, can be quite large. Indeed, in some aspects the load can be sufficient to intentionally exceed the yield strength of the component materials at predetermined locations, so that portions of the components can yield and slightly deform and compress together to become a more solidly locked assembly or unit. With the configuration of the universal capture portion 22 and receiver sub-assembly 14 shown in FIGS. 55-57, for example, the single load path 133 that extends downward from the concave lower surface 170 of the pressure insert 150 into the rounded outer surface 104 of the closed ring retainer 100 can cause the body of the retainer 100 to be slightly compressed in final locking, thereby clamping the upper portion of the universal capture portion 22 and preventing further rotation of the bone anchor 20 relative to the receiver 50.

Figure 58:
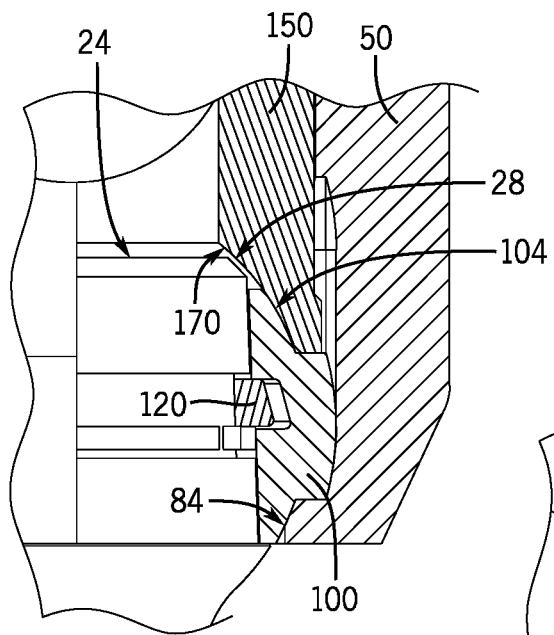
FIG. 58 is a close-up cross-sectional side view of the receiver sub-assembly and universal capture portion of FIG. 55, with the top edge surface of the universal capture portion engaging the concave lower surface of the pressure insert.

In another embodiment of the pivotal bone anchor assembly 10 shown in FIG. 58, the upper portion of the frusto-conical outer surface 30 of the universal capture structure 22 can be lengthened above the capture recess to the degree that the top edge surface 28 of the universal capture portion 22 extends sufficiently above the top edge surface 103 of the closed ring retainer 100 to become engaged by the concave lower surface 170 of the pressure insert 150 upon the coupling of the universal capture structure 22 with the closed ring retainer 100. As such, the concave lower surface 170 of the pressure insert 150 can engage with the chamfered or radiused top edge surface 28 of the universal capture portion 22 at the same time that it engages with the rounded outer surface 104 of the closed ring retainer 100.

Prior to final locking with the elongate rod and closure, this configuration of the universal capture portion 22 may remain rotatable within the closed ring retainer 100 about its longitudinal or spin axis prior to locking, but with a non-floppy friction fit caused by the top edge engagement that firmly holds the rotational position of the bone anchor 20 relative to the receiver sub-assembly 14, while still allowing for rotation of the bone anchor 20 about its longitudinal or spin axis with an applied force. In final locking, the additional engagement with the top edge 28 in this configuration can establish a second load path 135, in addition to the first load path 133, that extends downward from the elongate rod through the pressure insert 150, the capture portion 22, the snap ring 120, and the retainer 100 to the seating surface 84 and base 90 of the receiver 50, thereby splitting the applied load from the elongate rod. In this case the rotation of the bone anchor 20 can be constrained by both the clamping of the retainer 100 about the frusto-conical outer surface 30 as well as the additional friction engagement between the top edge surface 28 of the universal capture structure and the concave lower surface 170 of the pressure insert 150.

Figure 59:
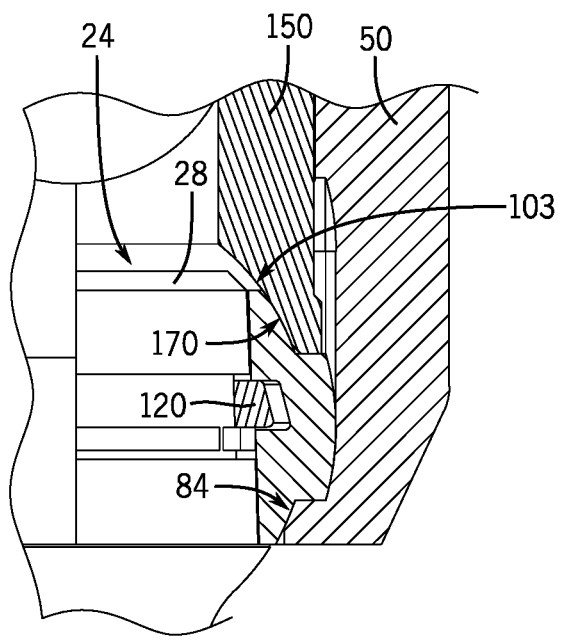
FIG. 59 is a close-up cross-sectional side view of the receiver sub-assembly and universal capture portion of FIG. 55, with the top edge surface of the universal capture portion extending above the top edge surface of the closed ring retainer.
Figure 60:
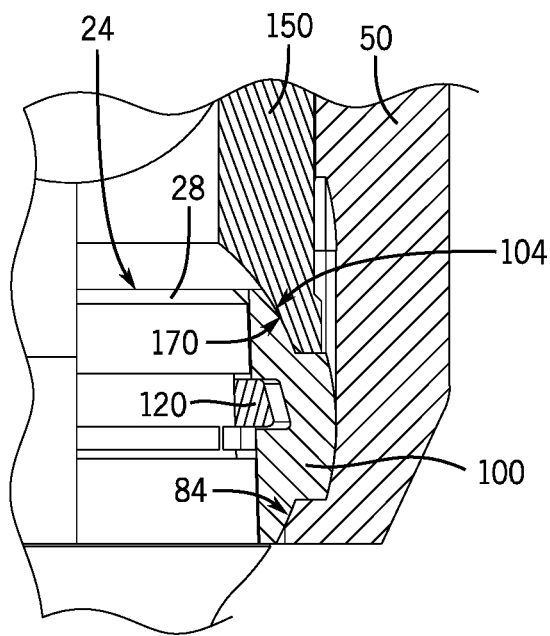
FIG. 60 is a close-up cross-sectional side view of the receiver sub-assembly and universal capture portion of FIG. 55, with the top edge surface of the universal capture portion being flush with the top edge surface of the closed ring retainer.

In yet additional embodiments of the pivotal bone anchor assembly, the top surface 24 and top edge surface 28 of the universal capture structure 22 can extend above the top edge surface 103 of the retainer 100 while still being spaced from the bottom surface 170 of the pressure insert 150, as shown in FIG. 59, or can be flush with the top edge surface 103 of the retainer 100, as shown in FIG. 60. As such, small gaps 136, 138 can be established between the two surfaces 28, 170 in these two configurations, respectively, that allows them to come into contact only during the final locking of the bone anchor assembly 12 as the internal components of the bone anchor assembly yield and slightly deform and compress together. Thus, it is foreseen that the size of the gap between the two surfaces 28, 170, as well as other dimensions of the various components of the receiver sub-assembly 14, can be used to control the loading characteristics of the bone anchor assembly 12 in the final locking state.

Figure 61:
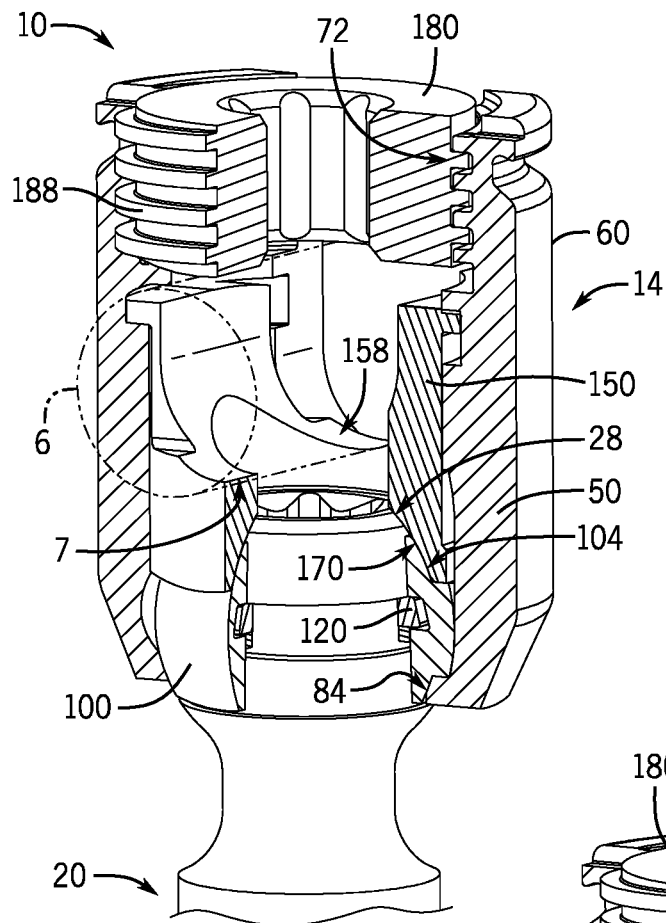
FIG. 61 is a partially cut-away front perspective view of the mono-planar pivotal bone anchor assembly, fully assembled with the elongate rod and closure and with the bone anchor in a non-articulated position relative to the receiver.
Figure 62:
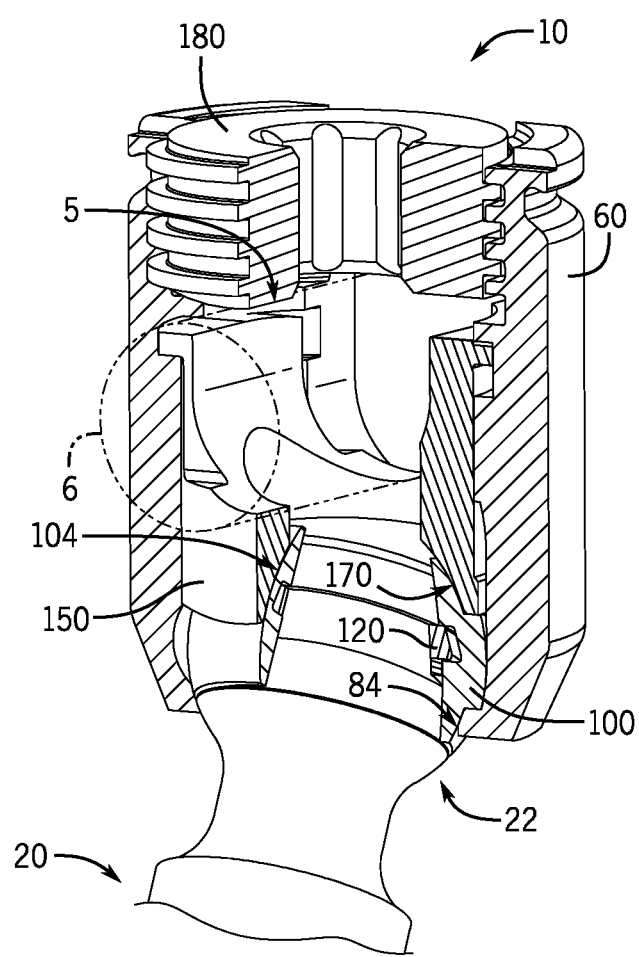
FIG. 62 is a partially cut-away front perspective view of the mono-planar pivotal bone anchor assembly, fully assembled with the elongate rod and closure and with the bone anchor in an articulated position relative to the receiver.

Illustrated in FIGS. 61-62 is the pivotal bone anchor assembly 10 as fully assembled and locked with the elongate rod 6 and a single-piece closure 180. For instance, after a desired alignment of the receiver sub-assembly to the bone anchor has been achieved, the elongate rod 6 can be installed (i.e. reduced) into the receiver channel 56, such as with instruments and/or breakoff extensions on the receiver 50, until the lowermost or underside surface 7 of the elongate rod 6 engages the inner upward-facing rod-seating surface 158 of the pressure insert 150. The closure 180 can then be installed into the upper portion of the central bore 70 of the receiver 50, in which the continuous guide and advancement structure 188 of the closure body engages the discontinuous guide and advancement structure 72 formed into the interior faces of the receiver upright arms 60. The closure 180 can be threaded downwardly until the bottom surface 184 of the closure 180 engages the top surface 5 of the elongate rod 6. Further rotation and torqueing of the closure 180 can then be used to drive the elongate rod 6 downward onto the pressure insert 150, which in turn drives the closed ring retainer 100 further downward into the partial spherical seating surface 84 in the receiver cavity 83 to achieve a final locking of the bone anchor assembly 10 in which the receiver sub-assembly 14 can no longer pivot to the universal bone anchor 20.

Furthermore, as the top edge surface 28 of the universal capture structure 22 extends above the top edge surface 103 of the closed ring retainer 100 to the extent that it is engaged by the rounded lower surface 170 of the pressure insert 150 in the locked configuration, the universal capture portion 22 will also become rotationally locked with the pressure insert 150 and receiver 50 at the same time that the closed ring retainer 100 is pivotably locked with the pressure insert 150 and receiver 50, even though there may be no rotational frictional engagement between the frusto-conical outer surface 30 of the universal capture portion 22 and the tapered inner surface 112 of the closed ring retainer 100.

Figure 63:
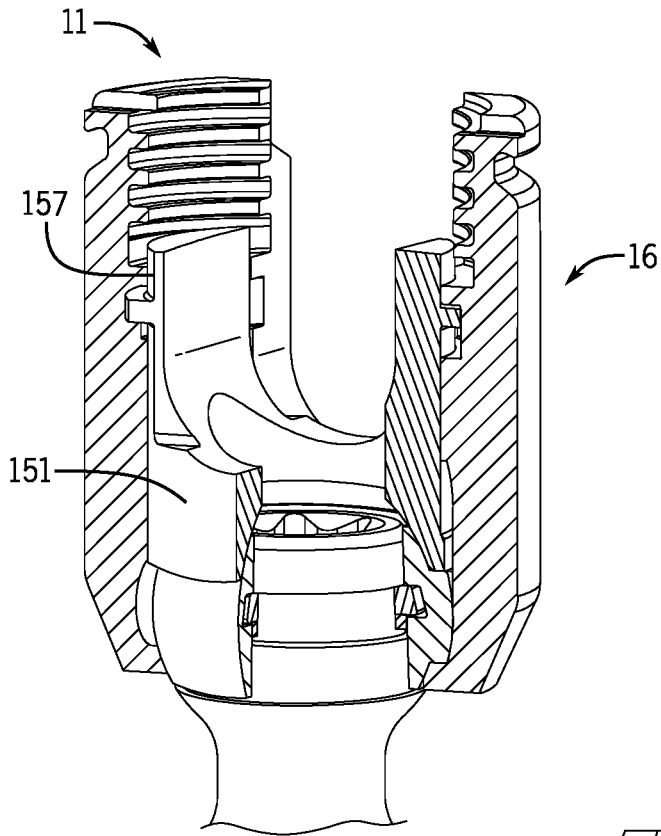
FIG. 63 is a partially cut-away front perspective view of a mono-planar receiver sub-assembly coupled with the universal capture portion of the bone anchor, in accordance with another representative embodiment of the present disclosure.
Figure 64:
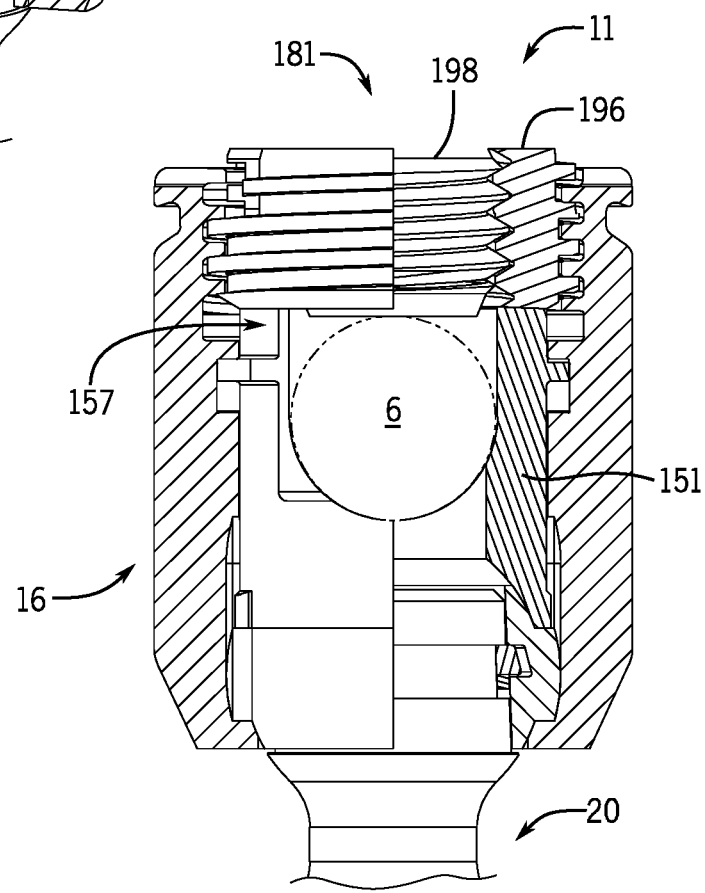
FIG. 64 is a partially cut-away front view of the fully assembled mono-planar pivotal bone anchor assembly of FIG. 63.

With reference to FIGS. 63-64, illustrated therein is another embodiment 11 of the mono-planar pivotal bone anchor assembly in which the two upright arms 157 of the pressure insert 151 can extend above a top surface 5 of the elongate rod 6, so as to be independently engageable by the outer ring 196 of a two-piece or "dual-innie" closure 181. An inner set screw piece 198 can be threaded downward through the central aperture of the outer ring 196 to separately engage and apply a locking pressure to the elongate rod 6 that independently secures or locks the elongate rod 6 to the receiver sub-assembly 16. This configuration can provide for independent positional or pivotable locking of the pivotal bone anchor assembly 11 without also locking the elongate rod 6, thereby allowing for some adjustment of the elongate rod 6 within the rod channel of the receiver prior to a final locking of the elongate rod 6 with the inner set screw 98.

In addition to the alternative embodiments discussed above, it is further foreseen that tooling may also be used in yet other embodiments of the pivotal bone anchor assembly to temporarily hold the pressure insert down in a locked position within the receiver sub-assembly, until there is a final locking of the pivotal bone anchor assembly with the elongate rod and via the closure.

A multi-planar pivotal bone anchor assembly 12 is shown in FIGS. 65-69, and in one aspect may only differ from the mono-planar embodiment 10 described above in that the mono-planar closed ring retainer 100 (having the opposing rounded outwardly-projecting protrusions or pegs 106, as shown in FIGS. 11-14) is replaced by a multi-planar closed ring retainer 101 having a rounded outer surface 105 that comprises a substantially continuous circumferential (i.e. without lateral protrusions) partial spherical outer surface, as shown in FIG. 67. All of the other components forming the multi-planar pivotal bone anchor assembly 12, including the universal shank 20, the scrapper ring 140, the snap ring 120, the pressure insert 150 (or 151), and the closure 180 (or 181) can be the same components as those described and illustrated above, so as to provide a modular spinal fixation system with all the attendant benefits described above.

Figure 68:
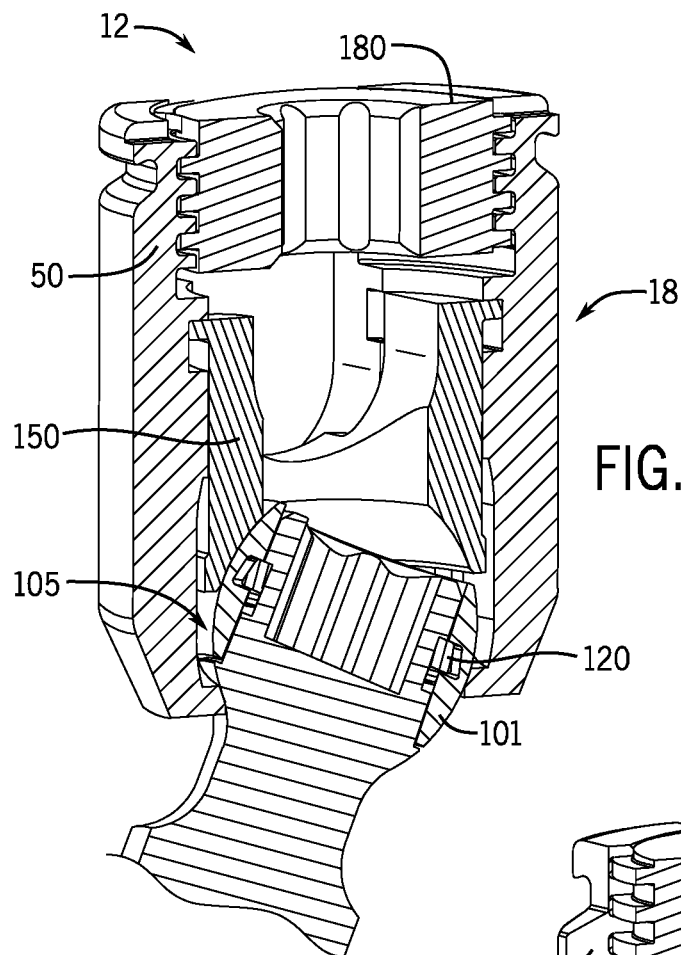
FIG. 68 is a partially cut-away front perspective view of the multi-planar pivotal bone anchor assembly of FIG. 65, fully assembled with the elongate rod and closure and with the bone anchor in an articulated position relative to the receiver.
Figure 69:
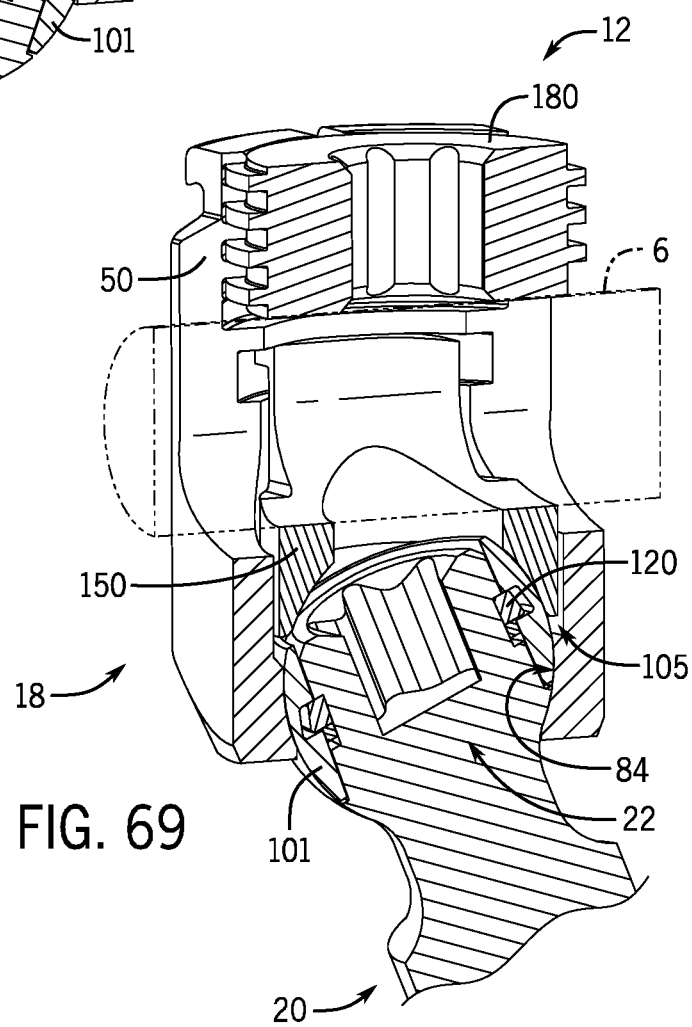
FIG. 69 is another partially cut-away front perspective view of the fully assembled multi-planar pivotal bone anchor assembly of FIG. 68 with the bone anchor in a different articulated position relative to the receiver.

With reference to FIG. 66, for example, the same receiver 50 having the opposed vertically-aligned recesses or pockets 86 formed into the cylindrical sidewall 80 of the central bore 70 and the upper portion of the partially spherical seating surface 84 can be used for both mono-planar receiver sub-assemblies 14 and multi-planar receiver sub-assemblies 16 without any decrease in performance. As with the mono-planar embodiment, the partial spherical outer surface 105 of the multi-planar closed ring retainer 101 is also slidably mateable with the inwardly-extending lower seating surface 84 proximate the bottom opening 94 of the receiver 50, only in this case to provide for polyaxial or multi-planar pivotal motion between the universal shank 20 and the multi-planar receiver sub-assembly 18 prior to locking the complete assembly 12 with the elongate rod 6 and closure 180. It will be appreciated, moreover, that the continuous 360-degree contact between the closed ring retainer 105 and the seating surface 84 generally avoids high-stress discontinuities while providing for a smooth continuous engagement between the internal components that resists pull-out at all angulation angles, as shown in FIGS. 68-69.

If desired, the receiver for the multi-planar embodiment may nevertheless be modified to only interface with the multi-planar closed ring retainer 105. This can be accomplished by eliminating the lower portions of vertically-aligned opposing pockets that extend into the lower seating surface of the receiver cavity, which in one aspect can provide for increased pull-out strength above that of the mono-planar bone anchor assembly. Nevertheless, the upper portions of the pockets 86 formed into the cylindrical sidewall 80 of the central bore 70 can remain so as to receive the opposed outwardly projecting nubs or protuberances 172 of the pressure insert 150 as it is rotated into position during assembly of the receiver sub-assembly, as described above.

As indicated above, the invention has been described herein in terms of preferred embodiments and methodologies considered by the inventor to represent the best mode of carrying out the invention. It will be understood by the skilled artisan, however, that a wide range of additions, deletions, and modifications, both subtle and gross, may be made to the illustrated and exemplary embodiments of the pivotal bone anchor assembly and spinal system without departing from the spirit and scope of the invention. As such, these and other revisions might be made by those of skill in the art without departing from the spirit and scope of the invention that is constrained only by the following claims.

What is claimed is:

1. A receiver assembly for securing an elongate rod to a bone anchor with a closure top, the bone anchor including a head portion and an anchor portion opposite the head portion configured for attachment to a bone of a patient, the receiver assembly comprising:

a receiver comprising a base defining a lower portion of a central bore centered about a centerline vertical axis and communicating with a bottom surface of the base through a bottom opening, and a pair of upright arms extending upward from the base having interior faces defining an open channel configured to receive the elongate rod, the central bore extending upward from the bottom opening through the open channel to tops of the upright arms and including:
- a circumferentially-extending support surface adjacent the bottom opening;
- a discontinuous guide and advancement structure adjacent the tops of the upright arms;
- a discontinuous inner recess with a downward-facing surface formed into the interior faces of the upright arms below the guide and advancement structure;
- a curvate sidewall surface extending between the inner recess and the support surface, and
- at least one side pocket recess formed into and entirely surrounded by the curvate sidewall surface at a location centered below the inner recess; and a pressure insert comprising a center aperture, a curvate rod-seating surface configured to receive at least an underside portion of the elongate rod, and an outer cylindrical surface sized to be slidably received within the central bore of the receiver, the pressure insert including:
- opposite flanges projecting radially outward from an upper portion of the outer cylindrical surface on either side of the rod-seating surface; and
- at least one side protuberance centered below one of the opposite flanges and projecting radially outward from a lower portion of the outer cylindrical surface below the opposite flanges, wherein the pressure insert is configured to be positioned into the central bore of the receiver in a first position with the rod-seating surface in non-alignment with the open channel of the receiver, and then rotated about the centerline vertical axis from the first position to a second position in which the rod-seating surface is in co-linear alignment with the open channel, and wherein upon the rotation of the pressure insert about the centerline vertical axis,
- the at least one side protuberance is interferingly forced across the curvate sidewall surface and into the at least one side pocket recess so as to inhibit further rotation of the pressure insert within the central bore, and
- the opposite flanges are rotated under the downwardly-facing surface of the inner recess so as to inhibit upward movement of the pressure insert within the central bore along the centerline vertical axis.

2. The receiver assembly of claim 1, wherein positioning the pressure insert into the central bore of the receiver in the first position further comprises downloading the pressure insert into the central bore through the open channel.

3. The receiver assembly of claim 1, further comprising a flattened zone formed into the curvate sidewall surface of the central bore laterally adjacent the at least one side pocket recess, wherein the flattened zone is configured to be increasingly frictionally engaged by the at least one side protuberance upon rotation of the pressure insert toward the second position.

4. The receiver assembly of claim 1,
wherein the at least one side pocket recess comprises a pair of opposing side pocket recesses centered below the inner recess formed into each upright arm, and
wherein the at least one side protuberance of the pressure insert comprises a pair of opposite nubs located proximate the lower bottom edge of the outer cylindrical surface.

5. The receiver assembly of claim 1, wherein the discontinuous guide and advancement structure comprises a helically-wound flangeform.

6. The receiver assembly of claim 1, wherein the discontinuous inner recess and the downward-facing surface of the central bore extend circumferentially around the central bore to opposing vertical planar side end surfaces formed into the interior faces of the channel that define the front and back ends of the channel.

7. The receiver assembly of claim 1, wherein the at least one side pocket recess comprises a vertically-elongate recess configured to provide for vertical movement of the pressure insert after the at least one side protuberance is rotated into the at least one side pocket recess.

8. A pivotal bone anchor assembly comprising the receiver assembly of claim 1 and the bone anchor, the head portion of the bone anchor including a lower spherical surface and an upper spherical surface,
wherein the head portion is configured for positioning within the lower portion of the central bore with the lower spherical surface pivotally engageable with the support surface of the receiver and the bone anchor extending downwardly through the bottom opening.

9. The pivotal bone anchor assembly of claim 8, wherein the pressure insert is configured to be positioned into the central bore of the receiver prior to the head portion of the bone anchor.

10. The pivotal bone anchor assembly of claim 8 and further comprising a retainer configured for positioning within the lower portion of the central bore, the retainer having a lower outer surface configured to engage the support surface of the central bore and an inner surface configured to capture and hold the head portion of the bone anchor within the base of the receiver.

11. The pivotal bone anchor assembly of claim 10, wherein the head portion of the bone anchor is uploadable into the lower portion of the central bore through the bottom opening of the receiver.

12. The pivotal bone anchor assembly of claim 11, wherein the retainer is positionable within the lower portion of the central bore prior to the head portion of the bone anchor.

13. The pivotal bone anchor assembly of claim 11,
wherein the support surface of the central bore further comprises a spherical seating surface adjacent the bottom opening, and
wherein the lower outer surface of the retainer further comprises a spherical surface configured to pivotably engage with the spherical seating surface to provide for pivotal motion between the receiver and the bone anchor.

14. A pivotal bone anchor assembly comprising the receiver assembly of claim 1, the bone anchor, and a retainer configured for positioning within the lower portion of the central bore, the retainer having a lower outer surface configured to engage the support surface of the central bore and an inner surface configured to capture and hold the head portion of the bone anchor within the base of the receiver.

15. The pivotal bone anchor assembly of claim 14 and further comprising the elongate rod and the closure top, wherein the closure top is configured for positioning entirely within the open channel of the receiver above the elongate rod and in engagement with the discontinuous guide and advancement structure to apply a downward pressure to a top of the elongate rod, so as to secure the elongate rod to the bone of the patient.

16. A receiver assembly for attachment to a head portion of a bone anchor prior to securing an elongate rod to the bone anchor with a closure top, the bone anchor including the head portion and an anchor portion opposite the head portion configured for attachment to a bone of a patient, the receiver assembly comprising:
 a receiver comprising a base portion defining a lower portion of a central bore centered about a centerline vertical axis and communicating with a bottom surface of the base portion through a bottom opening, and an upper portion having interior faces defining a channel configured to receive the elongate rod, the central bore extending upward from the bottom opening through the channel to a top of the upper portion and including:
  a circumferentially-extending support surface adjacent the bottom opening;
  a guide and advancement structure adjacent the top of the upper portion;
  a discontinuous inner recess with a downward-facing surface formed into the central bore below the guide and advancement structure; and
  at least one side pocket recess formed into and entirely surrounded by a curvate sidewall surface of the central bore between the inner recess and the support surface, and at a location centered below the inner recess, and
 a pressure insert comprising a center aperture, a curvate rod-seating surface configured to receive at least an underside portion of the elongate rod, and an outer cylindrical surface sized to be slidably received within the central bore of the receiver, the pressure insert further including:
  opposite flanges projecting radially outward from an upper portion of the outer cylindrical surface on either side of the rod-seating surface; and
  at least one side protuberance centered below one of the opposite flanges and projecting radially outward from a lower portion of the outer cylindrical surface below the opposite flanges,
 wherein the pressure insert is configured to be positioned into the central bore of the receiver in a first position with the rod-seating surface in non-alignment with the channel of the receiver, and then rotated about the centerline vertical axis from the first position to a second position in which the rod-seating surface is in co-linear alignment with the channel, and
 wherein upon the rotation of the pressure insert about the centerline vertical axis,
  the at least one side protuberance is interferingly forced across the curvate sidewall surface and into the at least one side pocket recess so as to inhibit further rotation of the pressure insert within the central bore, and
  the opposite flanges are rotated under the downwardly-facing surface of the inner recess so as to inhibit upward movement of the pressure insert within the central bore along the centerline vertical axis.

17. The receiver assembly of claim 16, wherein positioning the pressure insert into the central bore of the receiver in the first position further comprises downloading the pressure insert into the central bore through the channel.

18. The receiver assembly of claim 16, further comprising a flattened zone formed into the curvate sidewall surface of the central bore laterally adjacent the at least one side pocket recess, wherein the flattened zone is configured to be increasingly frictionally engaged by the at least one side protuberance upon rotation of the pressure insert toward the second position.

19. The receiver assembly of claim 16,
 wherein the at least one side pocket recess comprises a pair of opposing side pocket recesses centered below the inner recess formed into the central bore, and
 wherein the at least one side protuberance of the pressure insert comprises a pair of opposite nubs located proximate the lower bottom edge of the outer cylindrical surface.

20. The receiver assembly of claim 16, wherein the curvate sidewall surfaces of the central bore further comprise a partially discontinuous cylindrical surface extending between the inner recess and the support surface.

21. The receiver assembly of claim 16, further comprising a retainer configured for positioning within the lower portion of the central bore, the retainer having a lower outer surface configured to engage the support surface of the central bore and an inner surface configured to capture and hold the head portion of the bone anchor within the base portion of the receiver.

22. The receiver assembly of claim 21, where the retainer is positionable within the lower portion of the central bore prior to the head portion of the bone anchor.

23. The receiver assembly of claim 21,
 wherein the support surface of the central bore further comprises a spherical seating surface adjacent the bottom opening, and
 wherein the lower outer surface of the retainer further comprises a spherical surface configured to pivotably engage with the spherical seating surface to provide for pivotal motion between the receiver and the bone anchor.

24. A method of assembling a receiver assembly configured for attachment to a head portion of a bone anchor prior to securing an elongate rod to the bone anchor with a closure top, the bone anchor including the head portion and an anchor portion opposite the head portion configured for attachment to a bone of a patient, the method comprising:
 positioning a pressure insert into a first position in a central bore of a receiver,
  the receiver comprising a base defining a lower portion of the central bore centered about a vertical centerline axis and communicating with a bottom surface of the base through a bottom opening, and a pair of upright arms extending upward from the base having interior faces defining an open channel configured to receive the elongate rod, the central bore extending upward from the bottom opening through the open channel to tops of the upright arms and including:
   a circumferentially-extending support surface adjacent the bottom opening;
   a discontinuous guide and advancement structure adjacent the tops of the upright arms;
   a discontinuous inner recess with a downward-facing surface formed into the interior faces of the upright arms below the guide and advancement structure;
   a curvate sidewall surface extending between the inner recess and the support surface, and
   at least one side pocket recess formed into and entirely surrounded by the curvate sidewall surface at a location centered below the inner recess; and
  the pressure insert comprising a center aperture, a curvate rod-seating surface configured to receive at least an underside portion of the elongate rod, and an outer cylindrical surface sized to be slidably received within the central bore of the receiver, the pressure insert including:

opposite flanges projecting radially outward from an upper portion of the outer cylindrical surface on either side of the rod-seating surface; and at least one side protuberance centered below one of the opposite flanges and projecting radially outward from a lower portion of the outer cylindrical surface below the opposite flanges, wherein the rod-seating surface of the pressure insert is in non-alignment with the open channel of the receiver in the first position; and rotating the pressure insert about the centerline vertical axis from the first position to a second position in which the rod-seating surface is in co-linear alignment with the open channel, wherein upon the rotation of the pressure insert about the centerline vertical axis, the at least one side protuberance is interferingly forced across the curvate sidewall surface and into the at least one side pocket recess so as to inhibit further rotation of the pressure insert within the central bore, and the opposite flanges are rotated under the downwardly-facing surface of the inner recess so as to inhibit upward movement of the pressure insert within the central bore along the centerline vertical axis.

25. The method of claim 24, further comprising positioning a retainer into the lower portion of the central bore of the receiver, the retainer having a lower outer surface configured to engage the support surface of the central bore and an inner surface configured to capture and hold the head portion of the bone anchor within the base of the receiver.

26. The method of claim 25, further comprising uploading the head portion of the bone anchor through the bottom opening of the receiver after the retainer and the pressure insert have been positioned into the central bore and the pressure insert has been rotated to the second position, so as to form a fully-assembled pivotal bone anchor assembly configured for implantation into the bone of the patient.

27. The method of claim 25, further comprising uploading the head portion of the bone anchor through the bottom opening of the receiver after the retainer and the pressure insert have been positioned into the central bore and the pressure insert has been rotated to the second position, and prior to attachment of the anchor portion of the bone anchor to the bone of the patient, so as to form a pivotal bone anchor assembly configured for attachment to the bone of the patient.

28. The method of claim 25, further comprising uploading the head portion of the bone anchor through the bottom opening of the receiver after the retainer and the pressure insert have been positioned into the central bore and the pressure insert has been rotated to the second position, and the anchor portion of the bone anchor has been attached to the bone of the patient, so as to define a modular pivotal bone anchor assembly configured to secure an elongate rod to the bone anchor with a closure top.

\* \* \* \* \*